(12) United States Patent
Stein et al.

(10) Patent No.: US 6,511,973 B2
(45) Date of Patent: Jan. 28, 2003

(54) LACTAM INHIBITORS OF FXA AND METHOD

(75) Inventors: Philip D. Stein, Pennington, NJ (US); Yan Shi, Flourtown, PA (US); Stephen P. O'Connor, Newtown, PA (US); Chi Li, Randolph, NJ (US)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 09/916,941

(22) Filed: Jul. 27, 2001

(65) Prior Publication Data

US 2002/0045616 A1 Apr. 18, 2002

Related U.S. Application Data

(60) Provisional application No. 60/222,498, filed on Aug. 2, 2000.

(51) Int. Cl.⁷ .................... C07D 223/12; C07D 223/10; C07D 403/06; A61K 31/55
(52) U.S. Cl. .................... 514/212.03; 514/212.08; 540/524; 540/527
(58) Field of Search .............. 514/212.03, 212.08; 540/524, 527

(56) References Cited

U.S. PATENT DOCUMENTS

| | | | |
|---|---|---|---|
| 5,155,102 A | 10/1992 | Giannessi et al. | 514/212 |
| 5,340,798 A | 8/1994 | Nutt et al. | 514/18 |
| 5,484,917 A | 1/1996 | Lowe | 540/523 |
| 5,502,032 A | 3/1996 | Haupt et al. | 514/17 |
| 5,618,811 A | 4/1997 | Lowe | 514/218 |
| 5,672,598 A | 9/1997 | De et al. | 514/212 |
| 5,703,208 A | 12/1997 | Semple et al. | 530/331 |
| 5,932,733 A | 8/1999 | Semple et al. | 546/188 |
| 6,063,794 A | 5/2000 | Zhu et al. | 514/318 |
| 6,066,648 A | 5/2000 | Duggan et al. | 514/300 |

FOREIGN PATENT DOCUMENTS

| | | |
|---|---|---|
| EP | 0796855 A1 | 9/1997 |
| EP | 0761680 A2 | 12/1997 |
| WO | WO 93/01208 | 1/1993 |
| WO | WO 93/14113 | 7/1993 |
| WO | WO 94/09029 | 4/1994 |
| WO | WO 95/35311 | 12/1995 |
| WO | WO 95/35313 | 12/1995 |
| WO | WO 96/11940 | 4/1996 |
| WO | WO 96/29313 | 9/1996 |
| WO | WO 96/40679 | 12/1996 |
| WO | WO 97/14417 | 4/1997 |
| WO | WO 97/16425 | 5/1997 |
| WO | WO 97/30073 | 8/1997 |
| WO | WO 98/08840 | 3/1998 |
| WO | WO 98/12211 | 3/1998 |
| WO | WO 98/16523 | 4/1998 |
| WO | WO 98/16525 | 4/1998 |
| WO | WO 98/24784 | 6/1998 |
| WO | WO 98/35941 | 8/1998 |
| WO | WO 98/41510 | 9/1998 |
| WO | WO 98/56365 | 12/1998 |
| WO | WO 99/07731 | 2/1999 |
| WO | WO 99/07732 | 2/1999 |
| WO | WO 99/14191 | 3/1999 |
| WO | WO 99/30709 | 6/1999 |
| WO | WO 99/30713 | 6/1999 |
| WO | WO 99/52896 | 10/1999 |
| WO | WO 00/05208 | 2/2000 |
| WO | WO 00/08015 | 2/2000 |
| WO | WO 00/47207 | 8/2000 |
| WO | WO 00/47563 | 8/2000 |
| WO | WO 00/53264 | 9/2000 |

OTHER PUBLICATIONS

Lowe et al., Bioorganic & Medicinal Chem. Letter, vol. 4, No. 24, pp. 2877–2882, 1994.
Semple et al., J. Med. Chem., 1996, 39, 4531–4536.
Angelucci et al., Journal of Medicinal Chemistry, vol. 36, No. 11, May 28, 1993.
Sreenivasan et al., J. Med. Chem. 1993, 36, 256–263.
Skiles et al. Bioorganic & Medicinal Chem. Letters, vol. 3, No. 4, pp. 773–778, 1993.
Adang et al., Bioorganic & Medicinal Chem. Letters 8 (1998), 3603–3608.
Freidinger et al., J. Org. Chem., 1982, 47, 104–109.
Koomen et al., J.C.S. Perkin I (1973), p. 1934–1940.
Patent Abstracts of Japan, vol. 1997, No. 10, "Lactam Derivative and It's Salt", Fuji Yakuhin Kogyo KK.
Chemical Abstracts Service—"Syntheses of heterocycles, CCVIII." Database accession No. 90:121339 XP002178595.
Murakami et al., J. Med. Chem., 1999, 42, pp. 2621–2632.

*Primary Examiner*—Bruck Kifle
(74) *Attorney, Agent, or Firm*—Stephen B. Davis

(57) ABSTRACT

Compound of the formula

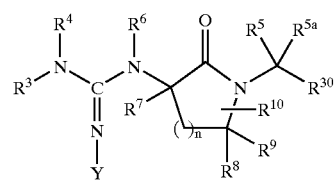

are inhibitors of the enzyme Factor Xa. These compounds are useful as anticoagulants in the treatment of cardiovascular diseases associated with thromboses.

7 Claims, No Drawings

LACTAM INHIBITORS OF FXA AND METHOD

This application claims priority to provisional U.S. Application No. 60/222,498 filed Aug. 2, 2000, the entirety of which is incorporated herein by reference.

FIELD OF THE INVENTION

The present invention relates to lactam inhibitors of the enzyme Factor Xa which are useful as anticoagulants in the treatment of cardiovascular diseases associated with thromboses.

BRIEF DESCRIPTION OF THE INVENTION

In accordance with the present invention, novel lactam derivatives are provided which are inhibitors of the enzyme Factor Xa and have the structure I

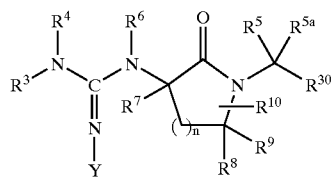

including pharmaceutically acceptable salts thereof and all stereoisomers thereof, and prodrugs thereof, wherein n is an integer from 1 to 5;

Y is selected from hydrogen, alkyl, substituted alkyl, alkenyl, substituted alkenyl, alkynyl, substituted alkynyl, aryl, cycloalkyl, heteroaryl, cycloheteroalkyl, cyano, nitro, hydroxy, amino, $-OR_a$, $-SR_a$,

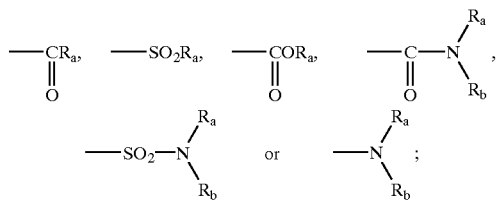

$R^4$, $R^6$, $R^8$, and $R^9$ are the same or different and are independently selected from hydrogen, alkyl, substituted alkyl, alkenyl, substituted alkenyl, alkynyl, substituted alkynyl, aryl, heteroaryl, cycloheteroalkyl, cycloalkyl, alkylcarbonyl, arylcarbonyl, cycloalkylcarbonyl, substituted alkyl-carbonyl, cycloheteroalkylcarbonyl and heteroarylcarbonyl;

$R^3$ is hydrogen, alkyl, substituted alkyl, alkenyl, substituted alkenyl, alkynyl, substituted alkynyl, aryl, heteroaryl, cycloalkyl, cycloheteroalkyl, cyano, nitro, hydroxy, $-OR_a$, $-SR_a$,

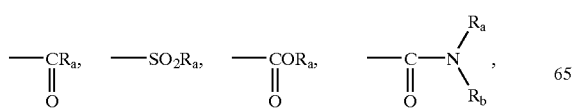

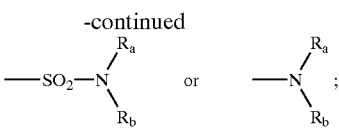

$R^5$, $R^{5a}$, and $R^7$ are the same or different and are independently selected from hydrogen, halogen, alkyl, substituted alkyl, alkenyl, substituted alkenyl, alkynyl, substituted alkynyl, heteroaryl, cycloalkyl, aryl, cycloheteroalkyl,

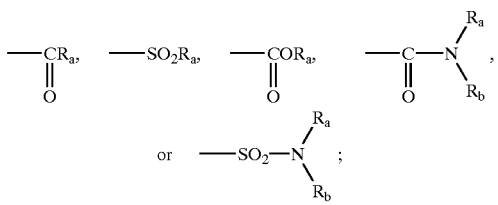

$R^{10}$ is selected from hydrogen, halogen, alkyl, substituted alkyl, alkenyl, substituted alkenyl, alkynyl, substituted alkynyl, aryl, heteroaryl, cycloalkyl, alkylcarbonyl, arylcarbonyl, cycloheteroalkyl, cycloalkylcarbonyl, substituted alkyl-carbonyl, cycloheteroalkylcarbonyl, heteroarylcarbonyl,

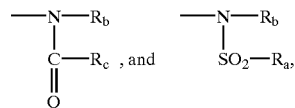

or when $R^9$ is hydrogen and $R^8$ and $R^{10}$ are on adjacent carbons they join to complete a cycloalkyl or phenyl ring;

$R^{30}$ is alkyl, substituted alkyl, alkenyl, substituted alkenyl, alkynyl, substituted alkynyl, heteroaryl, cycloalkyl, aryl, cycloheteroalkyl,

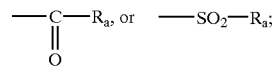

$R_a$ and $R_b$ are the same or different and are independently selected from hydrogen, alkyl, substituted alkyl, alkenyl, substituted alkenyl, alkynyl, substituted alkynyl, aryl, heteroaryl, cycloheteroalkyl, cycloalkyl, alkylcarbonyl, arylcarbonyl, cycloalkylcarbonyl, substituted alkyl-carbonyl, cycloheteroalkylcarbonyl, heteroarylcarbonyl, aminocarbonyl, alkylaminocarbonyl and dialkylaminocarbonyl;

$R_c$ is hydrogen, halogen, alkyl, substituted alkyl, alkenyl, substituted alkenyl, aryl, heteroaryl, cycloalkyl, cycloheteroaryl,

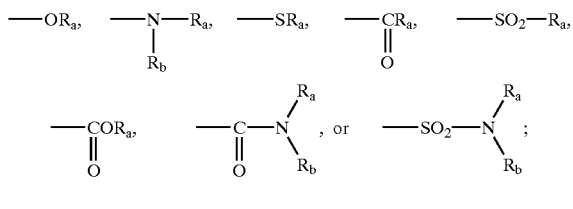

and wherein $R^3$ and $R^4$ and/or $R_a$ and $R_b$ can be taken together with the nitrogen to which they are attached, i.e.

to form a cycloheteroalkyl ring or a heteroaryl ring;

$R^3$ and Y can be taken together to form a heteroaryl ring;

$R^3$ or $R^4$ or Y can form a ring with $R^6$ which can be a cycloheteroalkyl or a heteroaryl ring;

$R^5$ and $R^{5a}$ can be taken together to the carbon to which they are attached to form a cycloalkyl ring, a heteroaryl ring or a cycloheteroalkyl ring; and where one or more of $R^3$ $R^4$ or $R^6$ are H, then double bond isomers are possible which are included in the present invention.

In addition, in accordance with the present invention, a method for preventing, inhibiting or treating cardovascular diseases associated with thromboses is provided, wherein a compound of formula I is administered in a therapeutically effective amount which inhibits Factor Xa.

DETAILED DESCRIPTION OF THE INVENTION

The following definitions apply to the terms as used throughout this specification, unless otherwise limited in specific instances.

The term "alkyl" or "alk" as employed herein alone or as part of another group includes both straight and branched chain hydrocarbons containing 1 to 20 carbons, preferably 1 to 12 carbons, more preferably 1 to 8 carbons in the normal chain. Examples include methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the various additional branched chain isomers thereof. The term "lower alkyl" includes both straight and branched chain hydrocarbons containing 1 to 4 carbons.

The term "alkenyl" as employed herein alone or as part of another group includes both straight and branched hydrocarbons having one or more double bonds, preferably one or two, and being of 2 to 20 carbons, preferably 2 to 12 carbons, and more preferably 2 to 8 carbons in the normal chain. Examples include

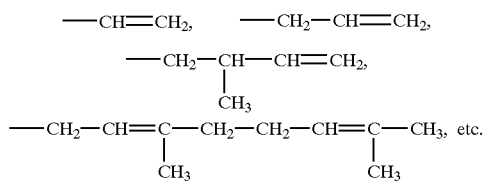

The term "alkynyl" as employed herein alone or as part of another group includes both straight and branched hydrocarbons having one or more triple bonds, preferably one or two, and being of 2 to 20 carbons, preferably 2 to 12 carbons, and more preferably 2 to 8 carbons in the normal chain. Examples include

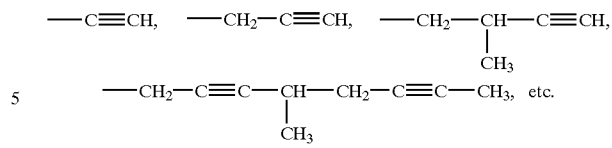

The terms "substituted alkyl", "substituted lower alkyl", "substituted alkenyl" and "substituted alkynyl", refer to such groups as defined above having one, two, or three substituents selected from halo, alkoxy, haloalkoxy, cycloalkyl, cycloheteroalkyl, aryl, heteroaryl, arylcycloalkyl, aryloxy, arylalkoxy, heteroaryloxo, hydroxy, —$N_3$, nitro, cyano, $(R_{20})(R_{21})N$—, carboxy, thio, alkylthio, arylthio, arylalkylthio, heteroarylthio, alkyl-C(O)—, alkoxycarbonyl, $(R_{20})(R_{21})N$—C(O)—, arylcarbonyloxy, alkyl-C(O)—NH—, alkyl-C(O)—N(alkyl)—, aryl-C(O)—NH—, aryl-C(O)—N(alkyl)—, aryl-C(O)—, arylalkoxycarbonyl, alkoxycarbonyl-NH—, alkoxycarbonyl-N(alkyl)—, cycloalkyl-C(O)—, cycloheteroalkyl-C(O)—, heteroaryl-C(O)—, cycloalkyl-C(O)—NH—, cycloalkyl-C(O)—N(alkyl), cycloheteroalkyl-C(O)—NH—, cycloheteroalkyl-C(O)—N(alkyl)—, heteroaryl-C(O)—NH—, heteroaryl-C(O)—N(alkyl)—, arylsulfinyl, alkylsulfinyl, cycloalkylsulfinyl, cycloheteroalkylsulfinyl, heteroarylsulfinyl, arylsulfonyl, alkylsulfonyl, cycloalkylsulfonyl, cycloheteroalkylsulfonyl, heteroarylsulfonyl, $(R_{20})(R_{21})N$-sulfinyl, $(R_{20})(R_{21})N$-sulfonyl, alkyl-$SO_2$—, NH—alkyl-$SO_2$—N(alkyl)—, aryl-$SO_2$—NH—, aryl-$SO_2$—N(alkyl)—, cycloalkyl-$SO_2$—NH—, cycloalkyl-$SO_2$—N(alkyl)—, cycloheteroalkyl-$SO_2$—NH—, cycloheteroalkyl-$SO_2$—N(alkyl)—, heteroaryl-$SO_2$—NH—, heteroaryl-$SO_2$—N(alkyl)—, $(R_{20})(R_{21})N$—C(O)—NH—, $(R_{20})(R_{21})N$—C(O)—N(alkyl)—, hydroxy-NH—C(O)—, hydroxy-N(alkyl)—C(O)—,

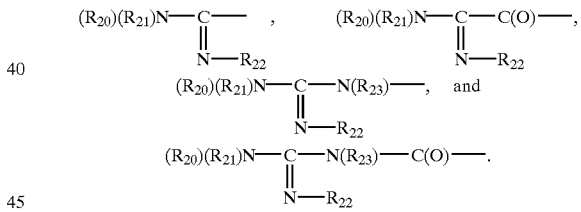

The term "cycloalkyl" as employed herein alone or as part of another group includes saturated or partially unsaturated (containing 1 or 2 double bonds and/or 1 or 2 triple bonds) cyclic hydrocarbon groups containing 1 to 3 rings, including monocyclicalkyl, bicyclicalkyl and tricyclicalkyl, containing a total of 3 to 20 carbons forming the rings, preferably 4 to 12 carbons forming the rings. Also included within the definition of "cycloalkyl" are such rings fused to an aryl, cycloheteroalkyl, or heteroaryl ring and bridged multicyclic rings containing 5 to 20 carbons, preferably 6 to 12 carbons, and 1 or 2 bridges. Examples include cyclopropyl, cyclobutyl, cyclopentyl, cyclohexyl, cycloheptyl, cyclooctyl, cyclodecyl and cyclododecyl, cyclohexenyl,

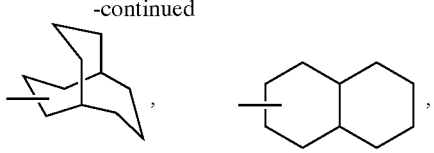

cyclopentenyl, cyclohexenyl, cycloheptenyl, cyclooctenyl, cyclohexadienyl, cycloheptadienyl, cyclopentynyl, cyclohexynyl, cycloheptynyl, cyclooctynyl, etc. Also included within the definition of "cycloalkyl" are such groups having one, two or three substituents selected from alkyl, substituted alkyl, halo, hydroxy, $(R_{20})(R_{21})N-$, alkoxycarbonyl, alkoxy, aryl, aryloxy, arylthio, heteroaryl and cycloheteroalkyl.

The term "aryl" as employed herein alone or as part of another group refers to phenyl, 1-naphthyl, and 2-naphthyl as well as such rings fused to a cycloalkyl, aryl, cycloheteroalkyl, or heteroaryl ring. Examples include

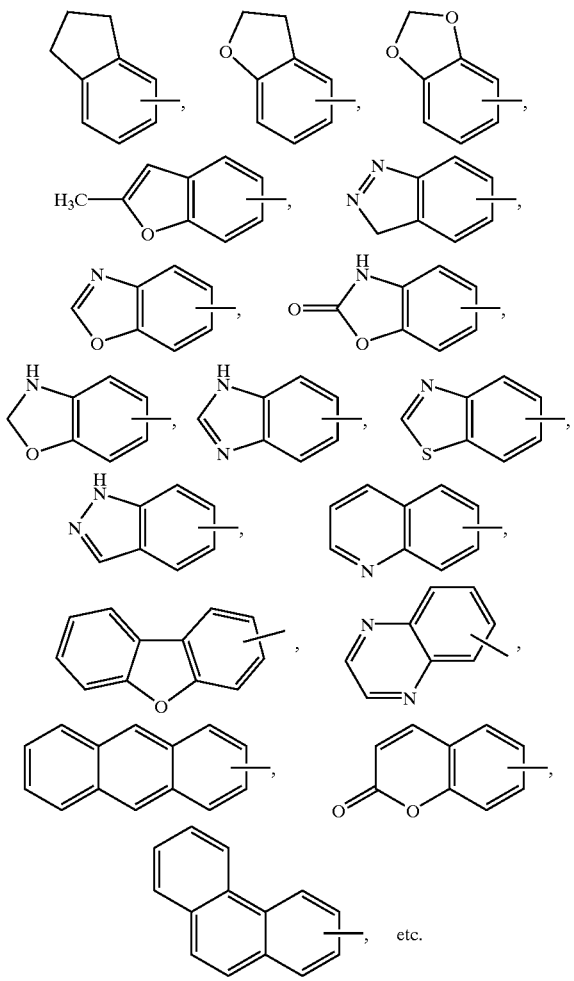

The term "aryl" also includes such ring systems wherein the phenyl, 1-naphthyl, or 2-naphthyl has one two, or three substitutents selected from halo, hydroxy, alkyl, alkenyl, alkoxy, haloalkoxy, carboxy, cyano, nitro, substituted alkyl, substituted alkenyl, alkylcarbonyl, (substituted alkyl) —C(O)—, aryloxy, arylalkoxy, arylthio, arylalkylthio, cycloheteroalkyl, heteroaryl, —N($R_{20}$)($R_{21}$), alkyl-SO$_2$—, (substituted alkyl)—SO$_2$—, aryl-SO$_2$—, cycloalkyl-SO$_2$—, cycloheteroalkyl-SO$_2$—, heteroaryl-SO$_2$—, alkyl-SO$_2$—NH—, aryl-SO$_2$—NH—, cycloheteroalkyl-SO$_2$—NH—, heteroaryl-SO$_2$—NH—, alkyl-SO$_2$—N(alkyl)—, (substituted alkyl)—SO$_2$—N(alkyl)—, cycloalkyl-SO$_2$—N(alkyl)—, aryl-SO$_2$—N(alkyl)—, cycloheteroalkyl-SO$_2$—N(alkyl)—, heteroaryl-SO$_2$—N(alkyl)—, ($R_{20}$)($R_{21}$)N—C(O)—, ($R_{20}$)($R_{21}$)N—C(O)—NH—, aryl-C(O)—, cycloalkyl-C(O)—, cycloheteroalkyl-C(O)—, heteroaryl-C(O)—, alkyl-O—C(O)—, substituted alkyl-O—C(O)—, cycloalkyl-O—C(O)—, aryl-O—C(O)—, heteroaryl-O—C(O)—, cycloheteroalkyl-O—C(O)—, alkyl-SO$_2$—O—, substituted alkyl-SO$_2$—O—, cycloalkyl-SO$_2$—, aryl-SO$_2$—O—, heteroaryl-SO$_2$—O—, cycloheteroalkyl-SO$_2$—O—, ($R_{20}$)($R_{21}$)—N—SO$_2$—O—, ($R_{20}$)($R_{21}$)—N—SO$_2$—, ($R_{20}$)($R_{21}$)N—C(O)—N(alkyl)—,

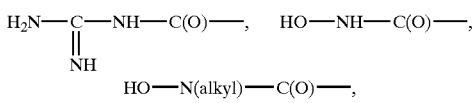

formyl, HC(O)—NH—, arylalkoxycarbonyl-NH—C(O)—, arylalkoxycarbonyl-N(alkyl)—C(O)—, ($R_{20}$)($R_{21}$)N—C(O)-alkyl-NH—C(O)—, ($R_{20}$)($R_{21}$)N—C(O)-alkyl-N(alkyl)—C(O)—, aryl-C(O)—NH—SO$_2$—, aryl-C(O)—N(alkyl)—SO$_2$—, cycloalkyl-C(O)—NH—SO$_2$—, cycloalkyl-C(O)—N(alkyl)—SO$_2$—, heteroaryl-C(O)—NH—SO$_2$—, cycloheteroalkyl-C(O)—NH—SO$_2$—, heteroaryl-C(O)—N(alkyl)—SO$_2$—, cycloheteroalkyl-C(O)—N(alkyl)—SO$_2$—, alkyl-C(O)—NH—SO$_2$—, alkyl-C(O)—N(alkyl)—SO$_2$—, substituted alkyl-C(O)—NH—SO$_2$—, substituted alkyl-C(O)—N(alkyl) -SO$_2$—, ($R_{20}$)($R_{21}$)N—C(O)-alkyl-NH—C(O)-alkyl-NH—C(O)—, ($R_{20}$)($R_{21}$)N—C(O)-alkyl-N(alkyl)—C(O)-alkyl-NH—C(O)—, and ($R_{20}$)($R_{21}$)N—C(O)-alkyl-NH—C(O)-alkyl-N(alkyl)—C(O)—, as well as pentafluorophenyl. Phenyl and substituted phenyl are the preferred aryl groups.

The term "cycloheteroalkyl" as used herein alone or as part of another group refers to 3-, 4-, 5-, 6- or 7-membered saturated or partially unsaturated rings which includes 1 to 2 hetero atoms such as nitrogen, oxygen and/or sulfur, linked through a carbon atom or an available nitrogen atom. Also included within the definition of cycloheteroalkyl are such rings fused to a cycloalkyl or aryl ring and spiro cycloheteroalkyl rings. One, two, or three available carbon or nitrogen atoms in the cycloheteroalkyl ring can be substituted with an alkyl, substituted alkyl, ($R_{20}$)($R_{21}$)N—, aryl, cycloalkyl, keto, alkoxycarbonyl, arylalkoxycarbonyl, alkoxycarbonyl-NH—, alkoxycarbonyl-N(alkyl)—, arylalkoxycarbonyl-NH-arylalkoxycarbonyl-N(alkyl)—, alkylcarbonyl-NH—, alkylcarbonyl-N(alkyl)—, arylcarbonyl, alkylsulfonyl, arylsulfonyl, substituted alkylsulfonyl, HO—N=, alkoxy-N=, (O)CH—, or ($R_{20}$)($R_{21}$)N—C(O)—. Also, an available nitrogen or sulfur atom in the cycloheteroalkyl ring can be oxidized. Examples of cycloheteroalkyl rings include

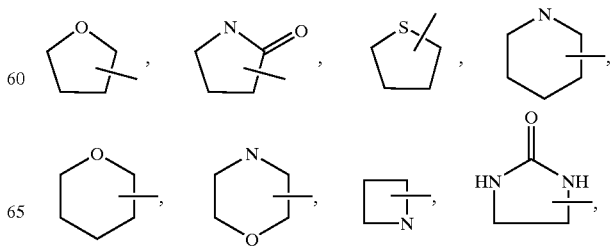

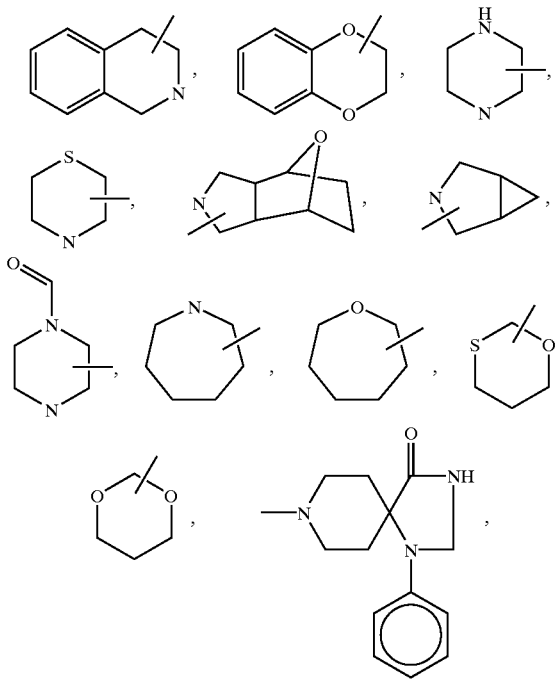

etc. Depending on the point of attachment, a hydrogen may be missing from the nitrogen atom in the above rings.

The term "heteroaryl", as used herein alone or as part of another group refers to a 5- 6- or 7- membered aromatic rings containing from 1 to 4 nitrotgen atoms and/or 1 or 2 oxygen or sulfur atoms provided that the ring contains at least 1 carbon atom and no more than 4 heteroatoms. The heteroaryl ring is linked through an available carbon or nitrogen atom. Also included within the definition of heteroaryl are such rings fused to a cycloalkyl, aryl, cycloheteroalkyl, or another heteroaryl ring. One, two, or three available carbon or nitrogen atoms in the heteroaryl ring can be substituted with an alkyl, substituted alkyl, alkoxy, alkylthio, keto, halo, hydroxy, cycloalkyl, aryl, cycloheteroalkyl, heteroaryl, $(R_{20})(R_{21})N—$, nitro, carboxy, cyano, alkoxycarbonyl, aryloxycarbonyl, alkylcarbonyl, substituted alkyl-C(O)—, arylcarbonyl, cycloalkylcarbonyl, $(R_{20})(R_{21})N—C(O)—$, guanidinylcarbonyl, $(R_{20})(R_{21})N—C(O)$-alkyl-NH—C(O)—, $(R_{20})(R_{21})N—C(O)$-alkyl-N(alkyl)—C(O)—, alkyl-C(O)—NH—, alkyl-C(O)—N(alkyl)—, substituted alkyl-C(O)—NH—, substituted alkyl-C(O)—N(alkyl)—, cycloalkyl-C(O)—NH—, cycloalkyl-C(O)—N(alkyl)—, aryl-C(O)—NH—, aryl-C(O)—N(alkyl)—, heteroaryl-C(O)—NH—, heteroaryl-C(O)—N(alkyl)—, cycloheteroalkyl-C(O)—NH—, cycloheteroalkyl-C(O)—N(alkyl)—, alkyl-SO$_2$—, substituted alkyl-SO$_2$—, aryl-SO$_2$—, cycloalkyl-SO$_2$—, cycloheteroalkyl-SO$_2$—, or heteroaryl-SO$_2$. Also an available nitrogen or sulfur atom in the heteroaryl ring can be oxidized. Examples of heteroaryl rings include

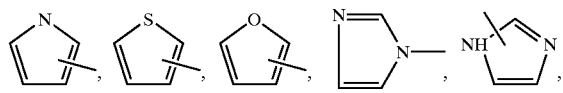

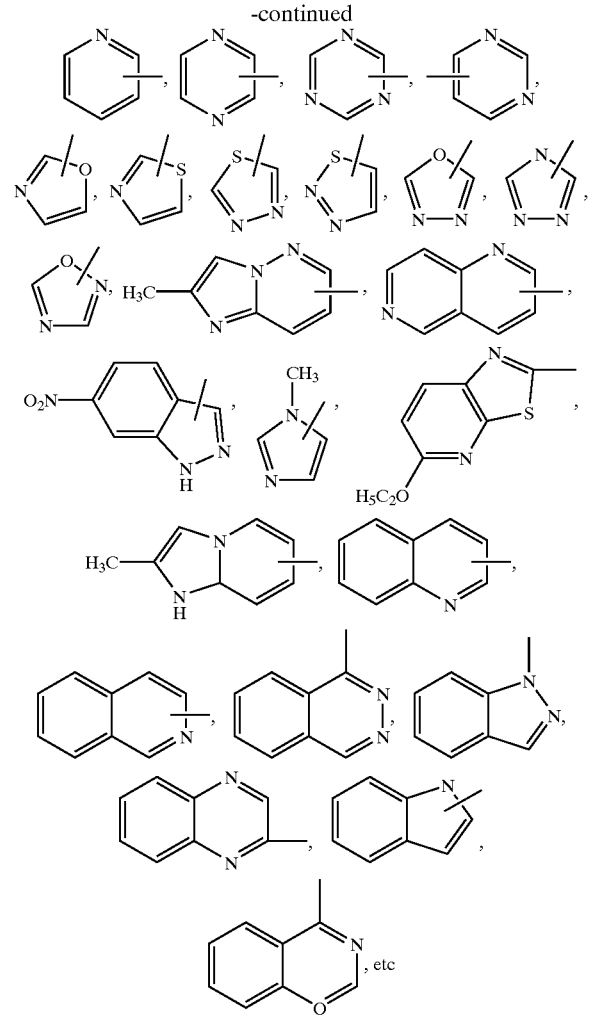

Again, depending on the point of attachment, a hydrogen may be missing from the nitrogen atom in the above rings.

The term "alkoxy" as employed herein alone or as part of another group includes "alkyl" groups as defined above bonded to an oxygen. Similarly, the term "alkylthio" as employed herein above or as part of another group includes "alkyl" groups as defined above bonded to a sulfur.

$R_{20}$, $R_{21}$, $R_{22}$ and $R_{23}$ are the same or different and are independently selected from hydrogen, alkyl, substituted alkyl, cycloalkyl, aryl, cycloheteroalkyl and heteroaryl.

The compounds of formula I can be prepared as salts, in particular pharmaceutically acceptable salts. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, with saturated or unsaturated dicarboxylic acids, for example oxalic, malonic, succinic, maleic, fumaric, phthalic or terephthalic acid, with hydroxycarboxylic acids, for example ascorbic, glycolic, lactic, malic, tartaric or citric acid, with amino acids, (for example aspartic or glutamic acid or lysine or arginine), or benzoic acid, or with organic sulfonic acids, such as $(C_1$–$C_4)$-alkyl- or arylsulfonic acids which are unsubstituted or substituted, for example by halogen, for example methane- or p-toluene sulfonic acid. Corresponding acid addition salts can also be formed if the compounds of formula I have an additional basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethylpropylamine, or a mono-, di- or trihydroxy lower alkylamine, for example mono-, di- or triethanolamine. Corresponding internal salts may furthermore be formed. Salts which are unsuitable for pharmaceutical uses but which can be employed, for example, for the isolation or purification of free compounds I or their pharmaceutically acceptable salts, are also included.

Preferred salts of the compounds of formula I include monohydrochloride, hydrogensulfate, methanesulfonate, phosphate or nitrate.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When enantiomeric or diastereomeric products are prepared, they can be separated by conventional methods for example, chromatographic or fractional crystallization.

It should be understood that the present invention includes prodrug forms of the compounds of formula I such as alkylesters of acids or any known prodrugs for lactam derivatives.

The compounds of the instant invention may, for example, be in the free or hydrate form, and may be obtained by methods exemplified by the following descriptions.

The compounds of formula I may be prepared by the exemplary processes described in the following reaction schemes. Exemplary reagents and procedures for these reactions appear hereinafter and in the working Examples.

In one method, lactam, II, is converted to IV by protection followed by substitution (via IIa) or by substitution followed by protection (via III). The CBZ protecting group or trifluoroacetyl group may be used in place of the BOC-group, for example.

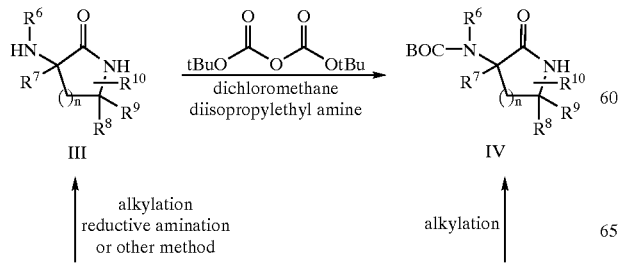

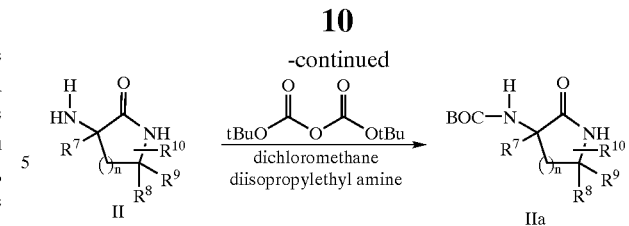

Compound IV is then converted to compound V by alkylation with halide VI. The protecting group is then removed from V by treatment with TFA to provide VII.

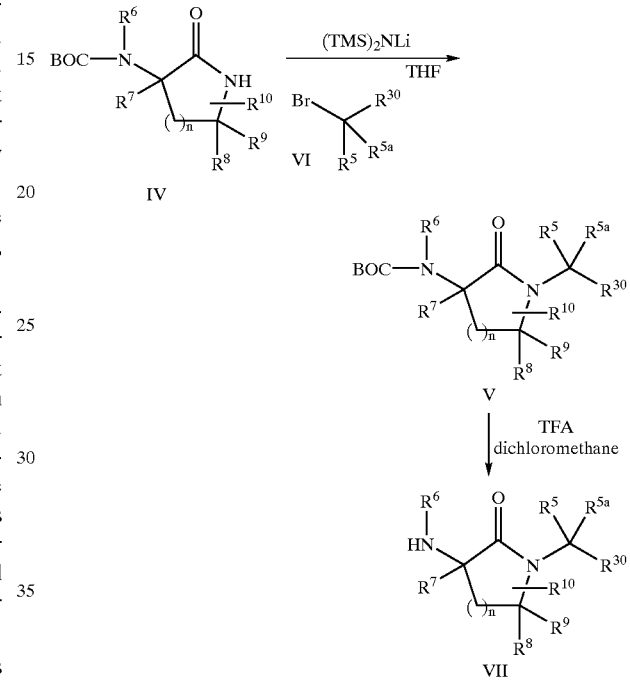

Compounds of type VII can then be converted to the target compounds as shown in the schemes below. In one method, an isothiocyanate VIII is converted to compound IX using sodium cyanamide. The salt IX is then coupled to compound VII by using 1-[3-(dimethylamino)propyl]-3-ethyl-carbodiimide (WSC or EDCI) in DMF to yield the targets.

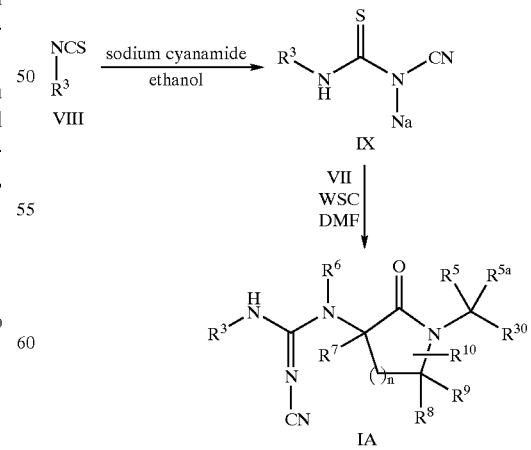

In another method, amine X is converted to intermediate XI by reaction with XII or XIII. Intermediate XI is then converted to target compounds IA by reaction in ethanol, ethyl acetate, DMF and the like. In the case where XI contains the MeS group, a mercury salt (such as mercuric acetate) can be used to speed the reaction.

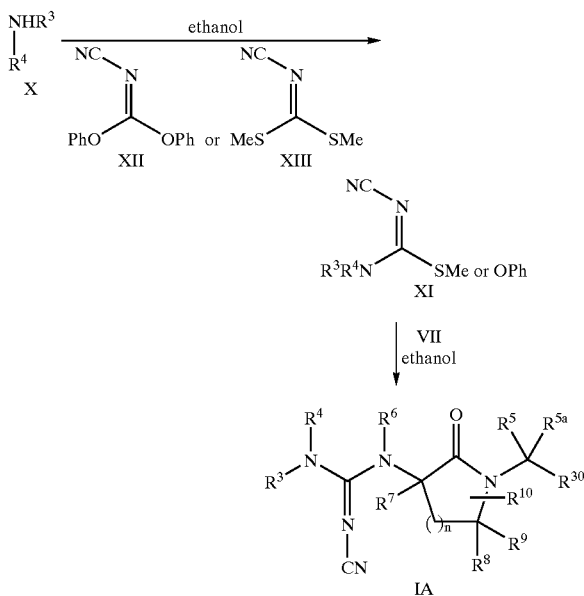

In another route, compound VII can be reacted with XII or XIII to prepare XIV. Compound XIV is then converted to IA by reaction with an amine in a solvent like acetonitrile or ethanol or DMF.

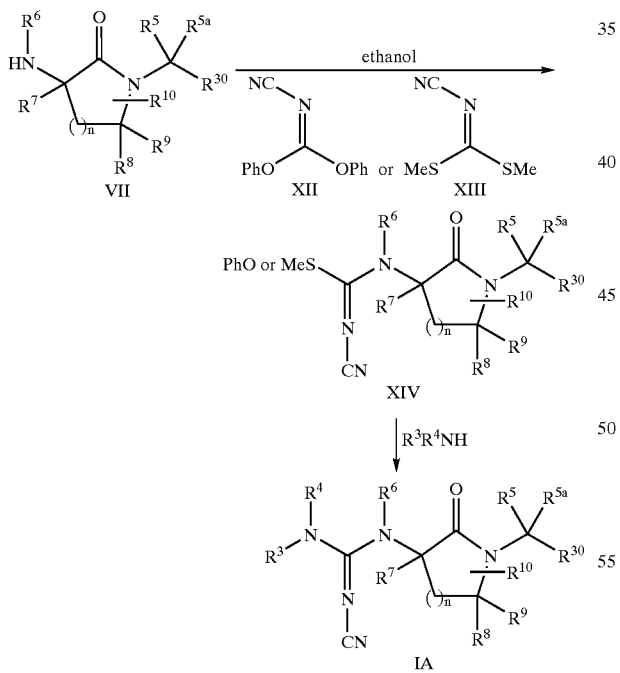

Compounds of the invention of type IB or IC can be prepared from thioureas of type XV. The reaction is carried out in the presence of a coupling agent such as ethyl 3-(dimethylamino)propylcarbodiimide hydrochloride (WSC, EDCI) or the like. Alternatively, the reaction can be carried out in the presence of a mercury salt (such as mercuric chloride, mercuric acetate, mercuric trifluoroacetate, mercuric oxide and the like) or salts of other metals such as silver, cadmium and the like.

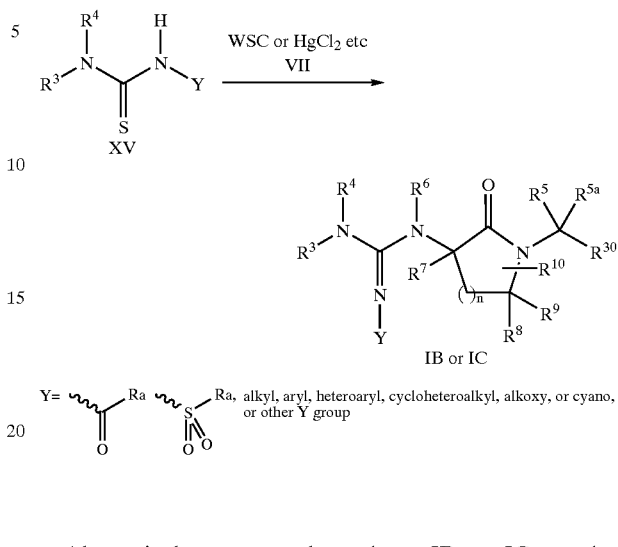

Alternatively, compounds such as IB or IC can be obtained from thioureas of type XVI in a similar manner.

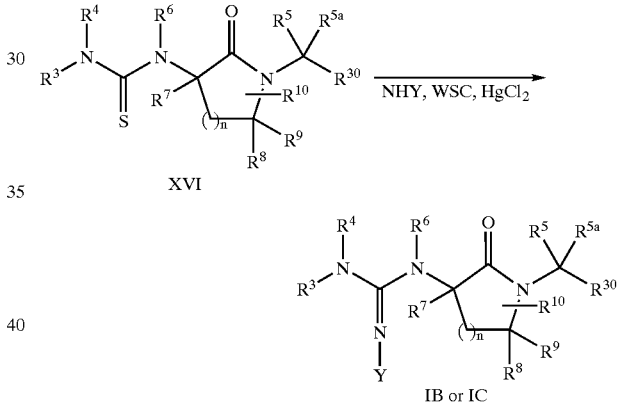

Thioureas of type XV and type XVI can be prepared by methods known in the literature. For example, an isothiocyanate can be reacted with a nitrogen-containing compound in an inert solvent (DMF, acetonitrile, THF, or the like) optionally in the presence of a base such as triethylamine, sodium hydride, tert-butylimino-tris(pyrrolidino) phosphorane, Hunig's base, and the like.

Alternatively, a multi-step procedure may be used to prepare compounds of type ID (where Y=Ra—C(O) ).

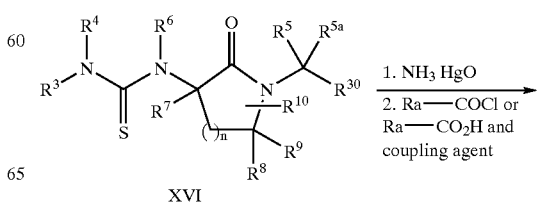

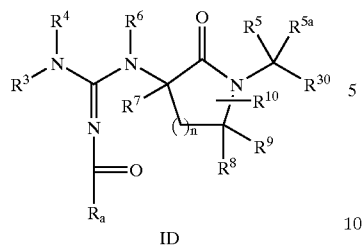

ID

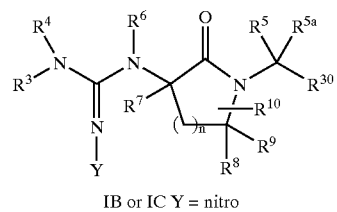

IB or IC Y = nitro

In addition, reagents such as XVII may be used as described above for the synthesis of compounds of type IB and IC

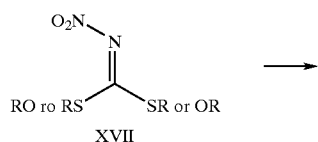

XVII

Other target compounds can also be prepared by converting compounds of type IV to esters of type XVIII as described above. These esters can be elaborated in similar manner to provide XIX. Conversion of the ester XVII to the acid XVIII can be accomplished, for example, by hydrogenation if $R^{11}$ is benzyl or by hydrolysis if $R^{11}$ is methyl, ethyl, or benzyl. Coupling and cyclization of XIX provides XX which can be transformed into IB or IC as described above.

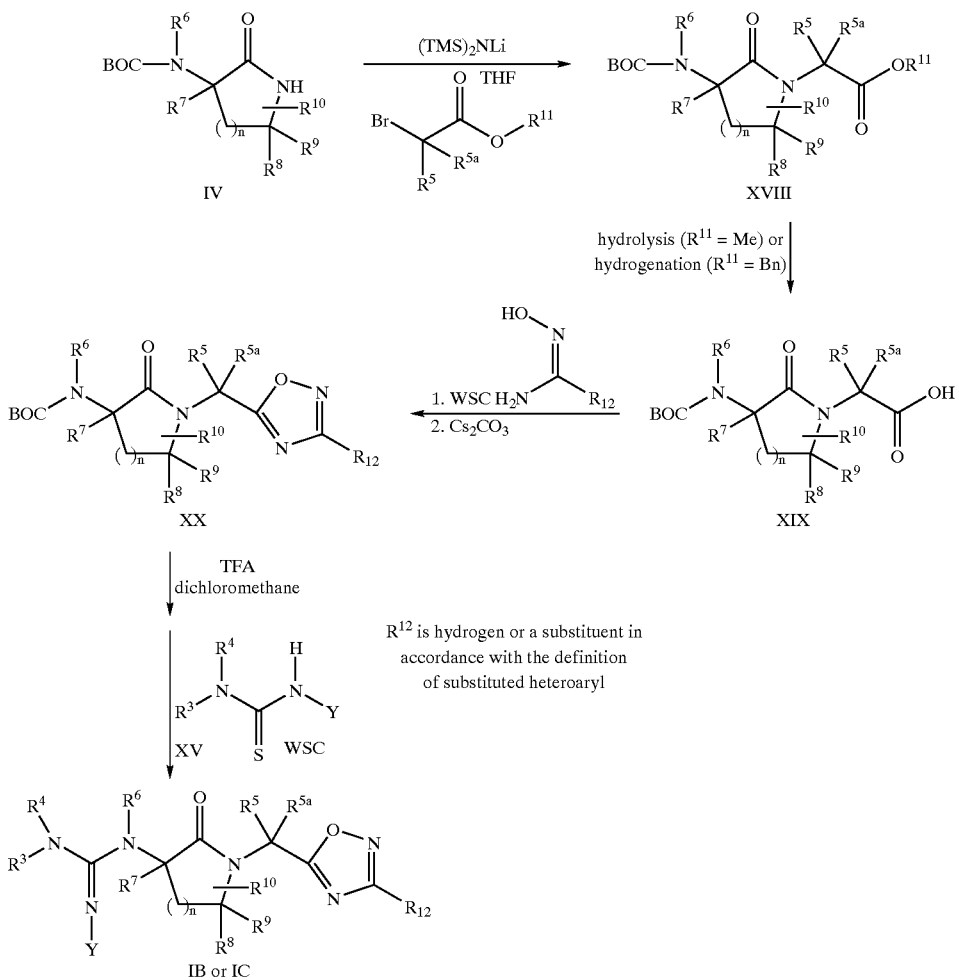

$R^{12}$ is hydrogen or a substituent in accordance with the definition of substituted heteroaryl Another subset of compounds of type I may be prepared by cycloaddition chemistry using intermediates which are prepared as described above.

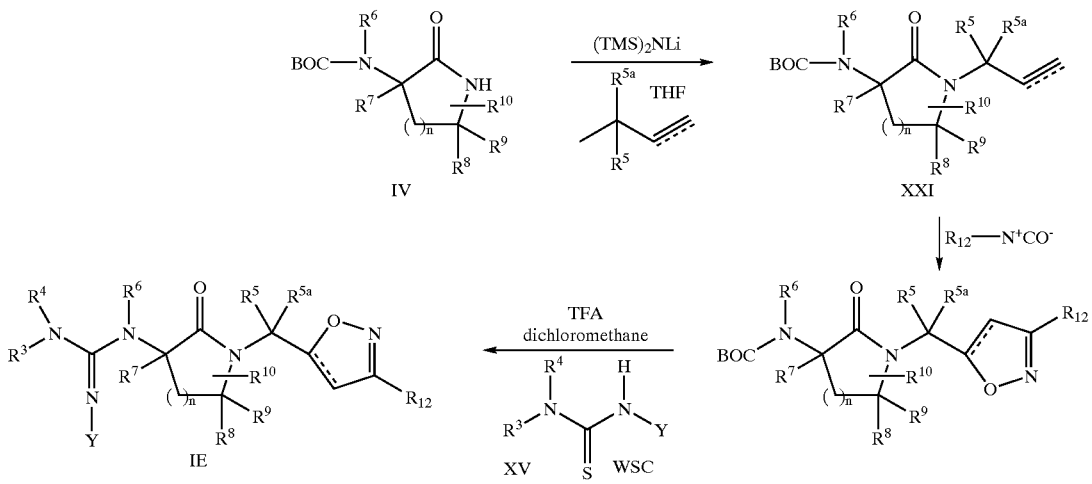

Preferred compounds of this invention are those of formula I including a pharmaceutically acceptable salt thereof wherein:

n is an integer from 1 to 4;
$R^3$ is hydrogen, alkyl, substituted alkyl, alkenyl, substituted alkenyl, aryl, heteroaryl or cycloheteroalkyl;
Y is cyano, nitro, aryl, heteroaryl, cycloheteroalkyl,

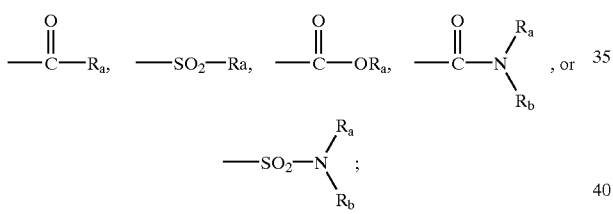

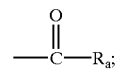

$R_a$ and $R_b$ are the same or different and are hydrogen, alkyl, substituted alkyl, alkenyl, substituted alkenyl, aryl, heteroaryl or cycloheteroalkyl;
$R^4$, $R^5$, $R^{5a}$, $R^6$, $R^7$, $R^8$, $R^9$ and $R^{10}$ are each hydrogen;
$R^{30}$ is alkyl, substituted alkyl, aryl, C(O)Ra, or heteroaryl and
the configuration at the chiral center is S— (as judged where $R^7$ is hydrogen).

The following compounds of formula I including a pharmaceutically acceptable salt thereof are more preferred:

n is 3 or 4, especially 3;
$R^3$ is aryl; especially a substituted benzofuranyl ring;
Y is cyano or $$-\overset{O}{\underset{\|}{C}}-R_a;$$

$R_a$ and $R_b$ are the same or different and are hydrogen, alkyl, aminocarbonyl, heteroaryl, aryl, or cycloheteroalkyl;
$R^4$, $R^5$, $R^{5a}$, $R^6$, $R^7$, $R^8$, $R^9$ and $R^{10}$ are each hydrogen;
$R^{30}$ is aryl, arylalkyl, C(O)-heteroaryl, C(O)aryl, substituted or unsubstituted isoxazol-5-yl, substituted or unsubstituted isoxazolin-5-yl, or substituted or unsubstituted 1,2,4-oxadiazol-5-yl and the configuration at the chiral center is S— (as judged where $R_7$ is hydrogen).

The following compounds of formula I including a pharmaceutically acceptable salt thereof are most preferred:

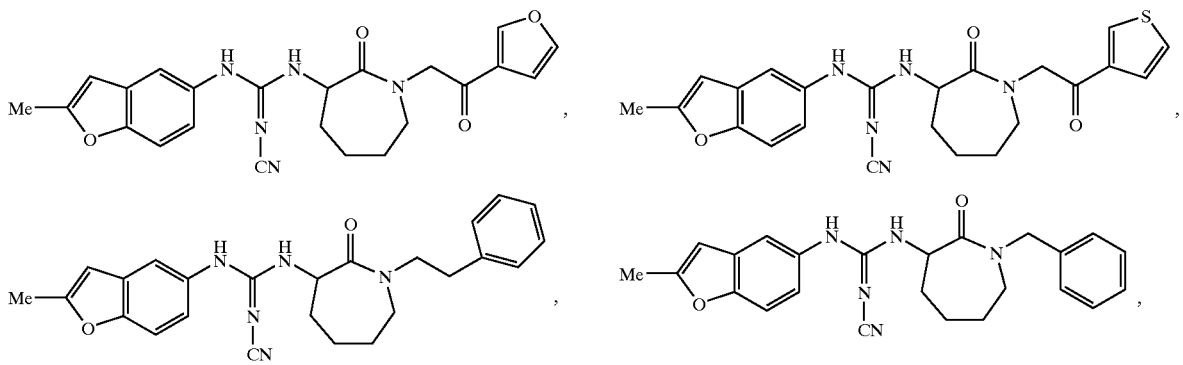

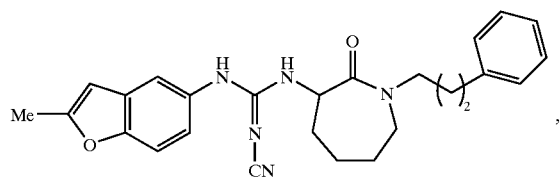
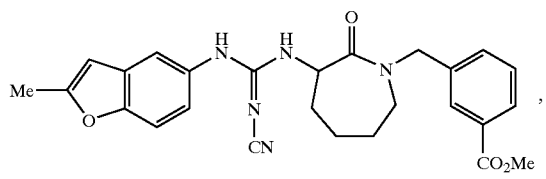
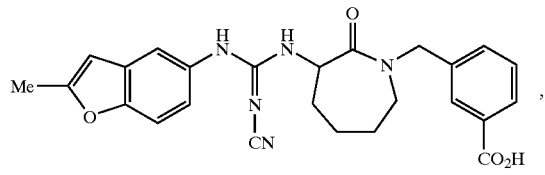
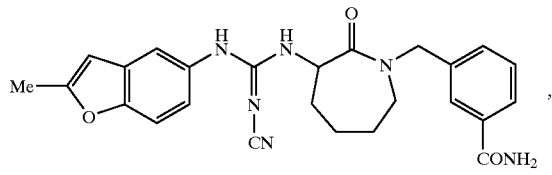
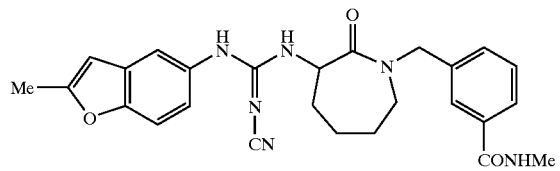
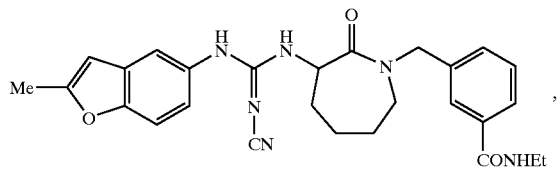
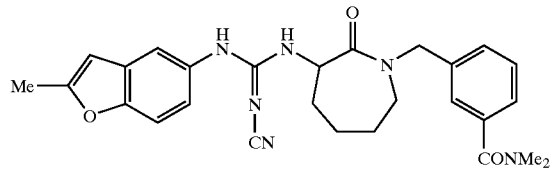
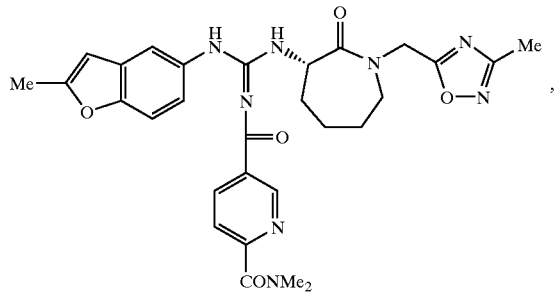
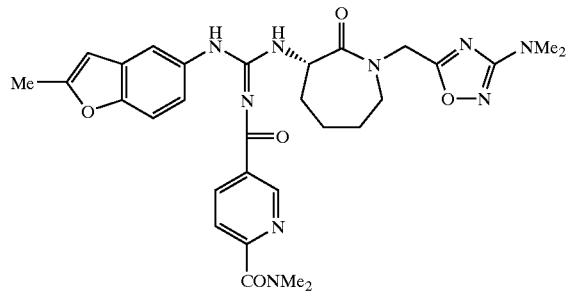
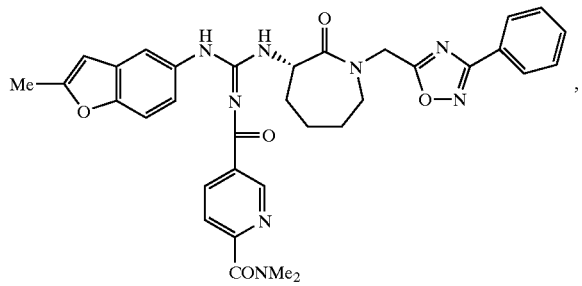
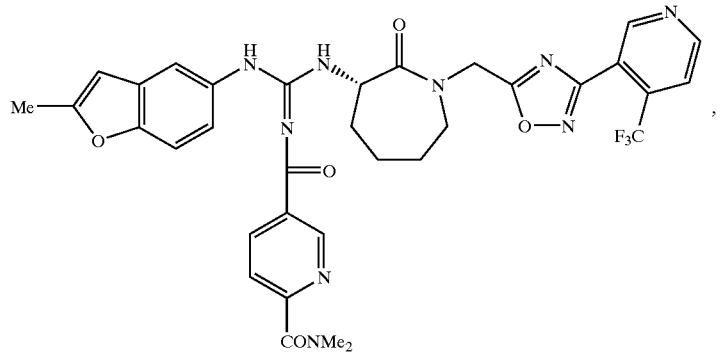

-continued

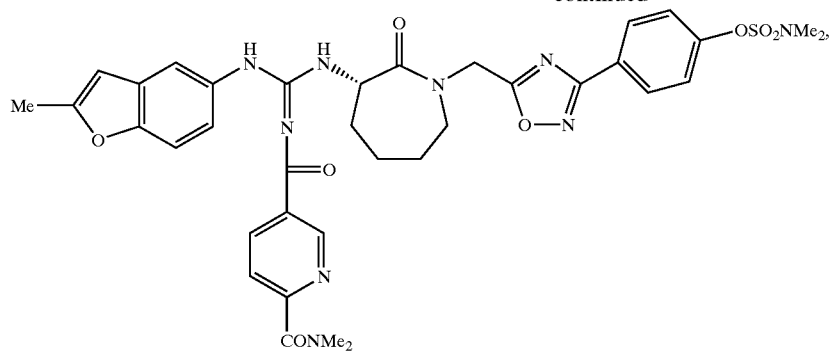

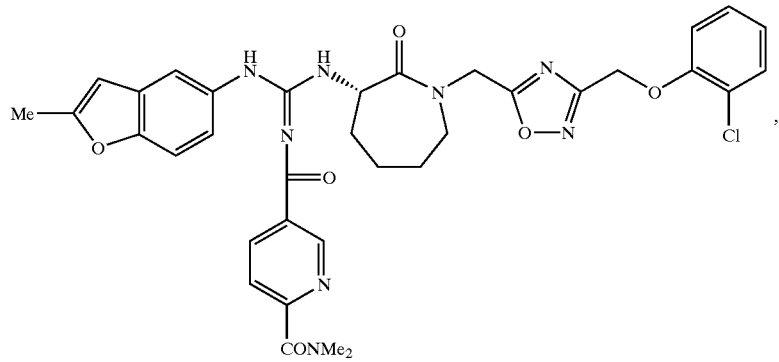

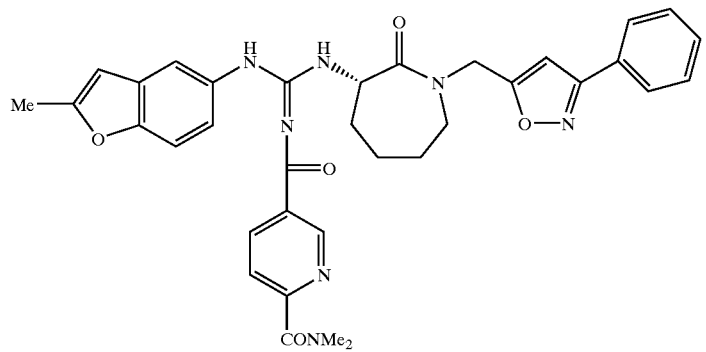

, and

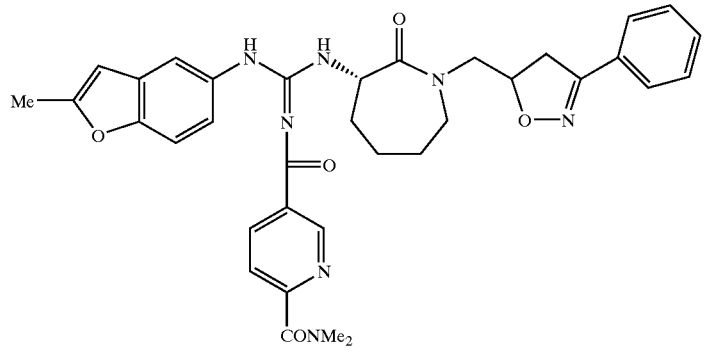

.

In the above formulas Me represents methyl and Et represents ethyl, and Ph represents phenyl.

Other methods used in the preparation of compounds of the invention are known to those skilled in the art and are not further described.

The compounds of the present invention are inhibitors of the activated coagulation serine protease known as Factor Xa and thus are useful to maintain the fluidity of blood. Additionally, compounds of the present invention are useful for the treatment or prophylaxis of Factor Xa-associated disorders. As used herein, the term "Factor Xa-associated disorder" refers to any disorder which may be prevented, partially alleviated or cured by the administration of a Factor Xa inhibitor. Thus, the compounds of the present invention are useful in the treatment or prevention of various Factor Xa-associated disorders including: Thrombotic or thromboembolic conditions; acute coronary syndromes (such as coronary artery disease, myocardial infarction (MI), unstable angina and non-Q Wave MI); thromboembolic stroke (such as that resulting from atrial fibrillation or from ventricular mural thrombus (low ejection fraction)); venous thrombosis (including deep vein thrombosis); arterial thrombosis; cerebral thrombosis; pulmonary embolism; cerebral embolism; peripheral occlusive arterial disease (e.g., peripheral arterial disease, intermittent claudication, critical leg ischemia, prevention of amputation, prevention of cardiovascular morbidity such as MI, stroke or death); thromboembolic consequenses of surgery, interventional cardiology or immobility; thromboembolic consequenses of medication (such as oral contraceptives, hormome replacement and heparin); thrombotic consequenses of atherosclerotic vascular disease and atherosclerotic plaque rupture leading to tissue ischemia; prevention of atherosclerotic plaque formation; transplant atherosclerosis; thromboembolic complications of pregnancy including fetal loss; thromboembolic consequences of thrombophilia (e.g., Factor V Leiden, and homocystinenimia); prothrombotic consequences and/or complications of cancer; prevention of thrombosis on artificial surfaces (such as stents, blood oxygenators, shunts, vascular access ports, vascular grafts, artificial valves, etc.); coagulopathies (e.g., disseminated intravascular coagulation (DIC)); coagulation syndromes; vascular remodeling atherosclerosis, restenosis and systemic infection; prevention of metastesis and tumor implantation; diabetic complications including retinopathy, nephropathy and neuropathy; inflammation; ischemia (such as that resulting from vascular occlusion, cerebral infarction, stroke and related cerebral vascular diseases); Kasabach-Merritt syndrome; atrial fibrillation; ventricular enlargement (including dilated cardiac myopathy and heart failure); restenosis (e.g., following arterial injury-induced either endogenously or exogenously).

Compounds of the present invention may additionally be useful as diagnostic agents and adjuncts. For example, the present compounds may be useful in maintaining whole and fractionated blood in the fluid phase such as required for analytical and biological testing. In addition, the compounds of the present invention may be useful for maintaining blood vessel patency in conjunction with vascular surgery including bypass grafting, arterial reconstruction, atherectomy, vascular graft and stent patency, organ, tissue and cell implantation and transplantation. In addition, the compounds of the present invention may be useful for maintaining blood vessel patency in conjunction with interventional cardiology or vascular surgery including bypass grafting, arterial reconstruction, atherectomy, vascular graft and stent patency, organ, tissue and cell implantation and transplantation.

The compounds of the present invention may be used in combination with each other, or with other Factor Xa inhibitors. Additionally, the present compounds may be used in combination with one or more of various other therapeutic agents, including: anti-arrythmic agents; anti-hypertensive agents; anti-platelet agents, anti-thrombotic and/or anti-thrombolytic agents; calcium channel blockers (L-type and T-type); cardiac glycosides; diruetics, mineralocorticoid receptor antagonists; phospodiesterase inhibitors; cholesterol/lipid lowering agents and lipid profile therapies; anti-diabetic agents; anti-depressants; anti-inflammatory agents (steroidal and non-steroidal); anti-osteoporosis agents; hormone replacement therapies; oral contraceptives; anti-coagulants; anti-obesity agents; anti-anxiety agents; anti-proliferative agents; anti-tumor agents; anti-ulcer and gastroesophageal reflux disease agents; growth hormone and/or growth hormone secretagogues; thyroid mimetics (including thyroid receptor antagonist); anti-infective agents; anti-viral agents; anti-bacterial agents; and anti-fungal agents.

Examples of suitable anti-arryhtmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K+ channel openers such as $I_{Ach}$ inhibitors, and $I_{Kur}$ inhibitors (e.g., compounds such as those disclosed in U.S. application Ser. No. 09/729,731, filed Dec. 5, 2000, WO 01/40231).

Examples of suitable anti-hypertensive agents for use in combination with the compounds of the present invention include: alpha adrenergic blockers; beta adrenergic blockers; calcium channel blockers (e.g. diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors)(e.g., omapatrilat and gemopatrilat); and nitrates.

Examples of suitable anti-platelet agents for use in combination with the compounds of the present invention include: GPIIb/IIIa blockers (e.g., abciximab, roxifiban, eptifibatide, tirofiban); $P2Y_{12}$ antagonists (e.g., clopidogrel, ticlopidine, CS-747); thromboxane receptor antagonists (e.g., ifetroban); aspirin; and PDE-III inhibitors (e.g., dipyridamole) with or without aspirin.

Examples of suitable anti-thrombotic and/or anti-thrombolytic agents for use in combination with the compounds of the present invention include: tissue plasminogen activator (natural or recombinant), tenecteplase (TNK), and lanoteplase (nPA); factor VIIa inhibitors; factor Xa inhibitors; thrombin inhibitors (such as hirudin and argatroban); PAI-1 inhibitors (i.e., inactivators of tissue plasminogen activator inhibitors); alpha2-antiplasmin inhibitors; streptokinase, urokinase and prourokinase; and anisoylated plasminogen streptokinase activator complex.

Examples of suitable calcium channel blockers (L-type or T-type) for use in combination with the compounds of the present invention include diltiazem, verapamil, nifedipine, amlodipine and mybefradil.

Examples of suitable cardiac glycosides for use in combination with the compounds of the present invention include digitalis and ouabain.

Examples of suitable diruetics for use in combination with the compounds of the present invention include: chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone.

Examples of suitable mineralocorticoid receptor antagonists for use in combination with the compounds of the present invention include sprionolactone and eplirinone.

Examples of suitable phospodiesterase inhibitors for use in combination with the compounds of the present invention include: PDE III inhibitors (such as cilostazol); and PDE V inhibitors (such as sildenafil).

Examples of suitable cholesterol/lipid lowering agents and lipid profile therapies for use in combination with the compounds of the present invention include: HMG-CoA reductase inhibitors (e.g., pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; cholesterol absorption inhibitors; and cholesterol ester transfer protein inhibitors (e.g., CP-529414).

Examples of suitable anti-diabetic agents for use in combination with the compounds of the present invention include: biguanides (e.g. metformin); glucosidase inhibitors (e.g. acarbose); insulins (including insulin secretagogues or insulin sensitizers); meglitinides (e.g. repaglinide); sulfonylureas (e.g., glimepiride, glyburide and glipizide); biguanide/glyburide combinations (e.g., Glucovance), thiozolidinediones (e.g. troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in U.S. Ser. No. 09/519,079 filed Mar. 6, 2000 (attorney docket LA27), glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protien tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-coagulants for use in combination with the compounds of the present invention include heparins (e.g., unfractioned and low molecular weight heparins such as enoxaparin and dalteparin).

Examples of suitable anti-obesity agents for use in combination with the compounds of the present invention include orlistat and aP2 inhibitors (such as those disclosed in U.S. Ser. No. 09/519,079 filed Mar. 6, 2000.

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, FK 506, and adriamycin.

Examples of suitable anti-tumor agents for use in combination with the compounds of the present invention include paclitaxel, adriamycin, epithilones, cisplatin, and carboplatin.

Examples of suitable anti-ulcer and gastroesophageal reflux disease agents for use in combination with the compounds of the present invention include famotidine, ranitidine, and omeprazole.

The various other therapeutic agents described above may be employed in the same dosage form with the compound of formula I or in different dosage forms, in dosages and regimens as generally known in the art or in the PDR.

The compounds of the present invention may act in a synergistic fashion with one or more of the above agents to prevent reocclusion following a successful thrombolytic therapy and/or reduce the time to reperfusion. The compounds of the present invention may also allow for reduced doses of the thrombolytic agent to be used and therefore minimize potential hemorrhagic side-effects.

The compounds of the present invention may also inhibit other serine proteases, for example, thrombin, Factor VIIa, urokinase-type plasminogen activator (urokinase), tryptase and/or trypsin. As a result, these compounds may additionally be useful as angiogenesis inhibitors in the treatment of cancer, as antiinflammatory agents particularly in the treatment of chronic asthma and in the treatment or prevention of allergic rhinitis, rheumatoid arthritis, inflammatory bowel disease, psoriasis, and conjunctivitis and in the treatment or prevention of pancreatitis.

The compounds of the invention can be administered orally or parenterally such as subcutaneously or intravenously, as well as by nasal application, rectally or sublingually to various mammalian species known to be subject to such maladies, e.g., humans, cats, dogs and the like in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

The active substance can be utilized in a composition such as tablet, capsule, solution or suspension or in other type carrier materials such as transdermal devices, iontophoretic devices, rectal suppositories, inhalant devices and the like. The composition or carrier will contain about 5 to about 500 mg per unit of dosage of a compound or mixture of compounds of formulas I, IA., IB, IC and ID. They may be compounded in conventional matter with a physiologically acceptable vehicle or carrier, excipient, binder, preservative, stabilizer, flavor, etc., as called for by accepted pharmaceutical practice.

The following working Examples represent preferred embodiments of the present invention.

General Experimental and definitions:
TFFH: Tetramethylfluoroformamidinium hexafluorophosphate. EDCI and WSC: 1-[3-(dimethylamino)propyl]-3-ethylcarbodiimide hydrochloride.
DMF: N,N-dimethylformamide
HPLC Methods:
Method 1: column—YMC ODS S-5, 4.6 mm×50 mm; flow—4 mL/min.; detection—220 nm; solvent-A—10% MeOH/water+0.2% phosphoric acid, B—90% MeOH/water+0.2% phosphoric acid; linear gradient—0% B to 100% B over 4 min then hold at 100% B for 2 min.
Method 2: identical to method 1 using a Phenom-Luna (ODS) S-5, 4.6 mm×50 mm column and with 1 min post-gradient hold.
Method 3: column—YMC ODS-A 4.6×50 mm I.D. S-3, 120 A; flow—2.5 mL/min.; detection—217 nm; solvent-A—90:10 water:MeOH+0.2% phosphoric acid, B—10:90 water:MeOH+0.2% phosphoric acid; linear gradient—0% B to 100% B over 8 min then hold at 100% B for 3 min.

Method 4: column—Phenom-LUNA 4.6×50 mm, S-5; flow—4 mL/min.; detection—220 nm; solvent-A—90:10 H20:MeOH+0.2% phosphoric acid, B—10:90 H20:MeOH+0.2% phosphoric acid; linear gradient—0% B to 100% B over 4 min then hold at 100% B for 1 min.

LCMS Conditions: Method 1: column—YMC ODS S-5, 4.6 mm×50 mm; flow—4 mL/min.; detection—220 nm; solvent-A—10% MeOH/water+0.1% TFA, B—90% MeOH/water+0.1% TFA; linear gradinet—0% B to 100% B over 4 min then hold at 100% B for 1 min.

Method 2: column—YMC ODS S-5, 4.6×33 mm; flow—5 mL/min; detection—220 nm; solvent-A—10% MeOH/water+0.1% TFA, B—90% MeOH/water+0.1% TFA; linear gradinet—0% B to 100% B over 2 min then hold at 100% B for 1 min.

EXAMPLE 1

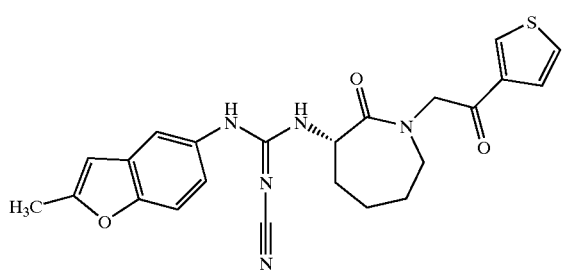

Part A:

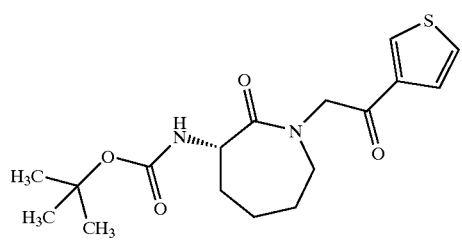

Lithium hexamethyldisilazide (1M in THF, 8 mL, 8 mmol) in tetrahydrofuran (4 mL) was added over 10 min to a stirring solution of 1,1-dimethylethyl [(3S)-hexahydro-2-oxo-1H-azepin-3-yl]carbamate (0.92 g, 4.0 mmol) in tetrahydrofuran (68 mL) under argon. The mixture was stirred at ambient temperature for 30 min, whereupon 2-bromo-1-(3-thienyl)ethanone (1.24 g, 6.0 mmol) in tetrahydrofuran (12 mL) was added over 3 min. After stirring at ambient temperature for 1.5 h, the reaction was quenched with 5% potassium hydrogensulfate and transferred to a separatory funnel with ethyl acetate. The mixture was extracted with ethyl acetate, washed with brine, dried over MgSO₄ and concentrated in vacuo to afford 2.1 g of crude product. Flash chromatography (silica, 25 mm dia column, 25% ethyl acetate/hexanes) afforded part A compound (0.44 g, 31%).

Part B:

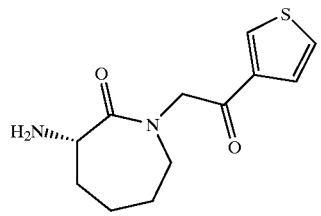

Trifluoroacetic acid (1.4 g, 0.94 mL, 12 mmol) was added to a solution of part A compound (0.44 g, 1.2 mmol) in dichloromethane (8 mL). After stirring at ambient temperature for 2 h, the reaction was evaporated in vacuo. The residue was dissolved in and then evaporated, sequentially, with dichloromethane (2×50 mL), methanol (50 mL) and dichloromethane (50 mL). This residue was taken up in methanol and chromatographed on BIORAD AG-50W×2 (hydrogen form, 9 g, prewashed with 20 mL each of methanol, water, 509 methanol/water). The column was washed with methanol (25 mL), and the compound was then eluted with 2N ammonia in methanol to afford the product as a dark red oil. Flash chromatography (silica, 15 mm dia column, 10% methanol/dichloromethane) of this residue afforded part B compound (0.24 g, 76%) as a yellow oil.

Part C:

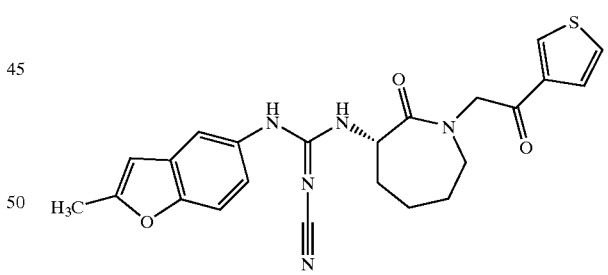

To 2-methyl-5-benzofuranamine (0.22 mmol) in DMF (0.35 mL) was added diphenyl cyanocarbonimidate (0.22 mmol). The mixture heated at 55° C. for 30 min. Part B compound (62 mg, 0.24 mmol) was added and the mixture was stirred at 55° C. for 1 day. Flash chromatography of entire reaction mixture (silica, 15 mm dia column, 2% methanol/dichloromethane) afforded the title compound (65 mg, 66% yield); LRMS (ESI, pos. ion spectrum) m/z 450 (M+H); HPLC (Method 1) $t_R$ 4.0 min.

EXAMPLE 2

Using the procedure described in Example 1 the following was prepared.

| Example | Structure | Characterization |
|---|---|---|
| 2 | 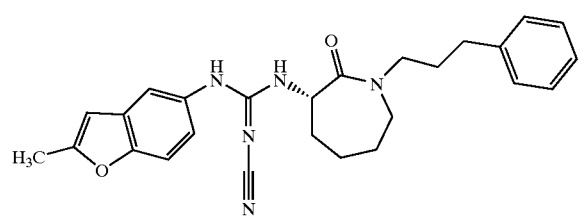 | HPLC (method SNB1) $t_R$ 4.2 min<br>LRMS (ESI, pos ion spectrum)<br>m/z 416 (M + H) |

EXAMPLE 3

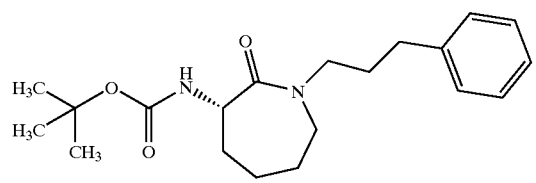

Part A:

A solution of 1,1-dimethylethyl [(3S)-hexahydro-2-oxo-1H-azepin-3-yl]carbamate (0.35 g, 1.5 mmol) in dimethylformamide (5 mL) was slowly added over 30 min to a suspension of sodium hydride (80% oil dispersion, 90 mg, 3 mmol) in dimethylformamide (25 mL) stirring at ambient temperature under argon. After stirring at ambient temperature for 30 min, a solution of (3-bromopropyl)benzene (0.45 mL, 3.5 mmol) in dimethylformamide (5 mL) was added. After stirring at ambient temperature for 3.5 h, the reaction was quenched with 5potassium hydrogensulfate and transferred to a separatory funnel with ethyl acetate. Extraction with ethyl acetate, washing with water and 10aqueous lithium chloride, and drying over $MgSO_4$ afforded 0.6 g of crude product. Flash chromatography (silica, 25 mm dia column, 20% ethyl acetate/hexane) afforded part A compound (0.38 g, 73%).

Part B:

From part A compound the title compound was prepared using procedures described in Example 1: LRMS (ESI, pos. ion spectrum) m/z 444 (M+H); HPLC (Method 1) $t_R$ 4.5 min.

Using the procedure described in Example 2 the following was prepared.

| Example | Structure | Characterization |
|---|---|---|
| 4 | 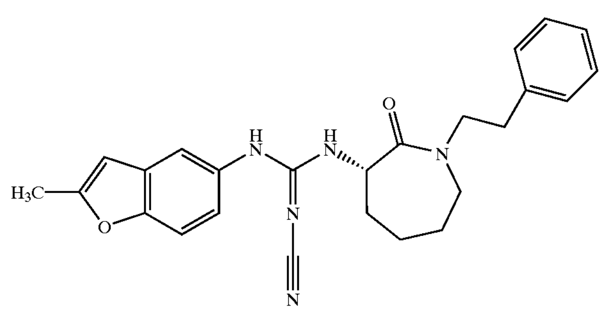 | HPLC (method 1)<br>$t_R$ 4.4 min<br>LRMS (ESI, pos ion spectrum)<br>m/z 430 (M + H) |

EXAMPLE 5

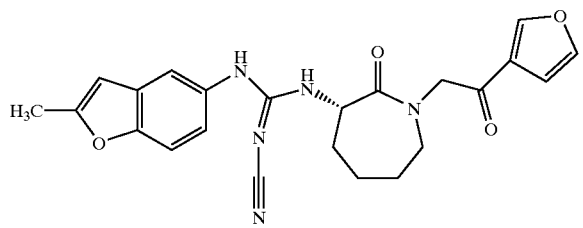

Part A:

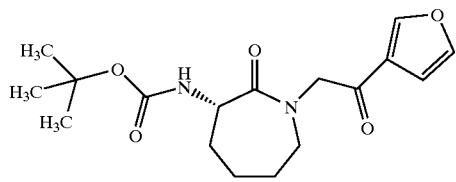

To a 50 mL round bottom flask charged with sodium hydride (0.15 g, 5.0 mmol) and DMF (10 mL) was added 1,1-dimethylethyl [(3S)-hexahydro-2-oxo-1H-azepin-3-yl] carbamate (0.57 g, 2.5 mmol). The reaction mixture was stirred under nitrogen at room temperature for 30 min. A solution of 2-bromo-1-(3-furanyl)ethanone (0.9 g 5, 5.0 mmol) in DMF (2 mL) was added to the reaction mixture slowly. The reaction mixture was stirred at room temperature for an additional one hour. The mixture was then was concentrated in vacuo. The residue was purified by flash chromatography (1:1 hexanes:ethyl acetate) to provide part A compound (0.19 g, 22% yield).

Part B:

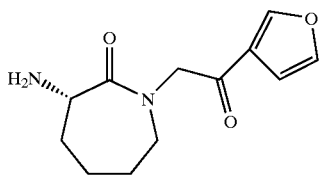

To a solution of compound part A (0.23 g, 1.0 mmol) and methylene chloride (2 mL) was added trifluoroacetic acid (1.0 mL, 7.0 mmol). The reaction mixture was stirred at room temperature for 16 h, and was then concentrated. The residue was taken up in methanol and loaded on a column of Biorad AG-50W×2 (hydrogen form, prewashed with water and methanol). The column was washed with methanol and then eluted with 2 N ammonia in methanol to provide part B compound (0.11 g, 67% yield).

Part C:

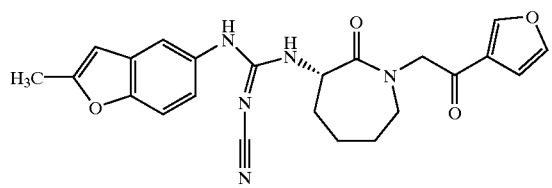

To 2-methyl-5-benzofuranamine (0.22 mmol) in DMF (0.35 mL) was added diphenyl cyanocarbonimidate (0.22 mmol). The mixture heated at 55° C. for 30 minutes. Part B compound (49 mg, 0.20 mmol) dissolved in DMF (1 mL) was added. The reaction mixture was stirred at 55° C. for 24 hours. The reaction mixture was diluted with ethyl acetate (50 mL). The organic layer was washed with brine (2×30 mL), dried over magnesium sulfate and concentrated in vacuo. Flash chromatography (silica gel, 2:1 hexanes/ethyl acetate) provided the title compound (42 mg, 48%) as a white solid: HPLC (method 4) $t_R$ 3.6 min; LCMS (ESI, pos. ion spectrum) m/z 434 (M+H)

EXAMPLE 6

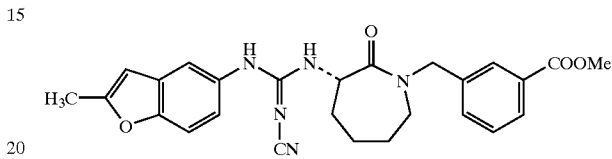

Using the method described in Example 5, the title compound was prepared: HPLC (method 4) $t_R$ 4.0 min; LCMS (ESI, pos. ion spectrum) m/z 474 (M+H).

EXAMPLE 7

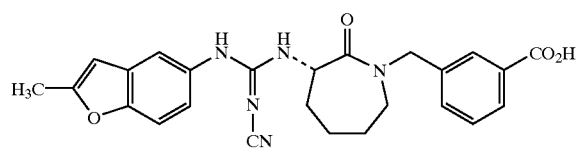

The compound of example 6 (510 mg, 1.07 mmol) was dissolved in THF (10 mL) and 8.6 mL of 2.5 M LiOH aqueous solution was added. The reaction mixture was stirred at room temperature for 24 hours. The reaction mixture was concentrated by rotary evaporation and the residue was dissolved in methylene chloride. The organic mixture was extracted with water (2×25 mL). The combined aqueous layers were brought to pH 4 with 1 N HCl. The resultant aqueous mixture was then was extracted with ethyl acetate (2×25 mL). The combined ethyl acetate extracts were dried over $Na_2SO_4$ and concentrated to give the title compound (490 mg, 100%): HPLC (method 4) $t_R$ 3.8 min; LCMS (ESI, pos. ion spectrum) m/z 460 (M+H).

EXAMPLE 8

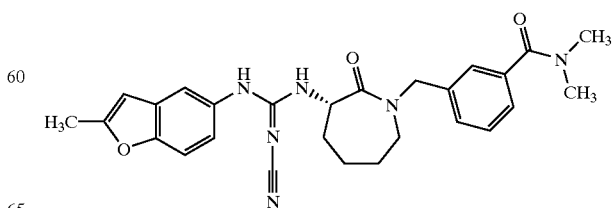

The compound of Example 7 (46 mg, 0.10 mmol) was dissolved in XX mL of DMF, then TFFH (26 mg, 0.10 mmol) and Et₃N (0.020 mL, 0.14 mmol) were added. The reaction mixture was stirred at room temperature for 30 min. Then 2 M dimethyl amine in THF (0.060 mL, 0.12 mmol) was added, and the reaction mixture was continued stirring at room temperature for another 2 hours. The reaction mixture was diluted with ethyl acetate (20 mL). The organic solution was washed with brine (2×20 mL) and concentrated. The residue was purified by preparative HPLC (C-18 column; solvent A—90:10 water:MeOH+0.20% TFA and solvent B—10:90 water:MeOH+0.2% TFA) to provide the title compound (XXX mg, XXX%): HPLC (method 4) $t_R$ 3.6 min; LCMS (ESI, pos. ion spectrum) m/z 487 (M+H).

EXAMPLES 9–11

Using the procedure described in Example 8, the following were prepared.

| example | structure | characterization |
|---|---|---|
| 9 | 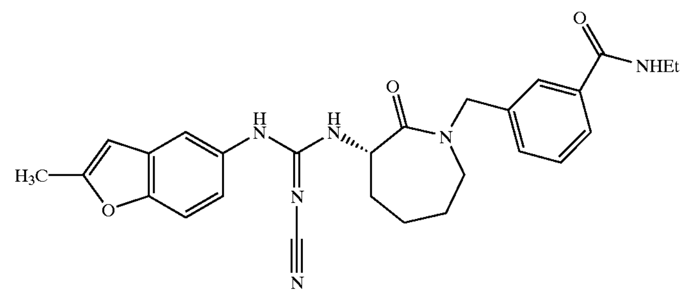 | HPLC (method 3) $t_R$ 3.7 min LCMS (ESI, pos. ion spectrum) m/z 487 (M + H) |
| 10 | 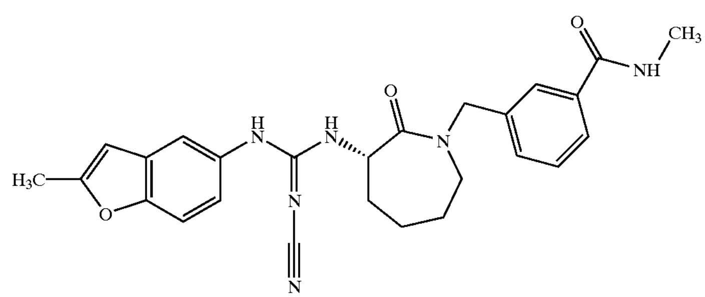 | HPLC (method 3) $t_R$ 3.6 min LCMS (ESI, pos. ion spectrum) m/z 473 (M + H) |
| 11 | 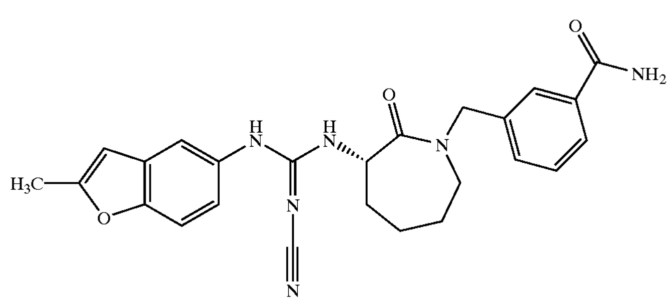 | HPLC (method 3) $t_R$ = 3.5 min LCMS (ESI, pos. ion spectrum) m/z 459 (M + H) |

EXAMPLE 12

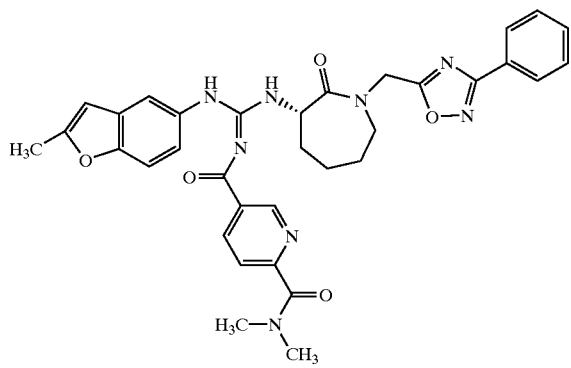

Part A:

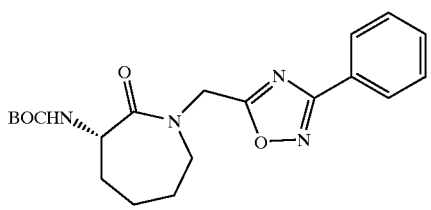

A solution of (3S)-3-[[(1,1-dimethylethoxy)-carbonyl]amino]hexahydro-2-oxo-1H-Azepine-1-acetic acid (0.10 g, 0.35 mmol), 1-[3-(dimethylamino)propyl]-3-ethylcarbodiimide hydrochloride (170 mg, 0.58 mmol), and 1-hydroxybenzotriazole (49 mg, 0.36 mmol) in dichloromethane (1.5 mL) and dimethylformamide (0.40 mL) was stirred at ambient temperature for 30 min. N-hydroxybenzenecarboximidamide (48 gm, 0.35 mmol) in dichloromethane (0.5 mL) was then added. After stirring at ambient temperature for 1.5 h, the reaction was transferred to a separatory funnel with dichloromethane and 0.1N hydrochloric acid. The mixture was extracted with dichloromethane (2×). The combined organic layers were washed with saturated sodium bicarbonate and brine, dried over magnesium sulfate and concentrated in vacuo to afford 0.14 g of crude material.

This residue was then dissolved in tetrahydrofuran (2.5 mL) and cesium carbonate (0.25 mg, 0.75 mmol) was added. After stirring at 50° C. for 3 h, the reaction was transferred to a separatory funnel with dichloromethane and 0.1 N hydrochloric acid. The mixture was extracted with dichloromethane (2×). The combined organic layers were washed with saturated sodium bicarbonate and brine, dried over magnesium sulfate and concentrated in vacuo to afford 0.14 g of crude product. Flash chromatography (silica, 15 mm dia column, 35% ethyl acetate/hexane) afforded part A compound (100 mg, 76w): HPLC (Method 1) 10 $t_R$ 3.9 min; LCMS (ESI, pos ion spectrum, method 1) m/z 387 (M+H), $t_R$ 3.80 min.

Part B:

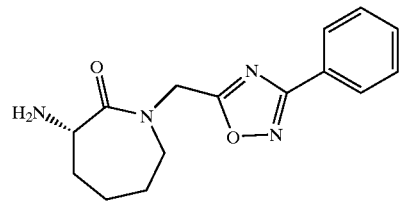

A solution of part A compound (100 mg, 0.27 mmol) in dichloromethane (0.80 mL) and trifluoroacetic acid (0.40 mL) was stirred at ambient temperature. After 1 h, the reaction was evaporated in vacuo. The residue was coevaporated with dichloromethane (2×), methanol and dichloromethane to afford crude product (120 mg). This residue was taken up in methanol and added to a column of AG 50W-X2 (200–400 mesh, 3.0 g, prewashed with 8 mL each of methanol, water, and 1/1 methanol/water). The column was washed with methanol (8 mL) and eluted with 2 N ammonia in methanol to afford part B compound (58 mg, 76%): HPLC (Method 1) $t_R$ 2.3 min.

Part C:

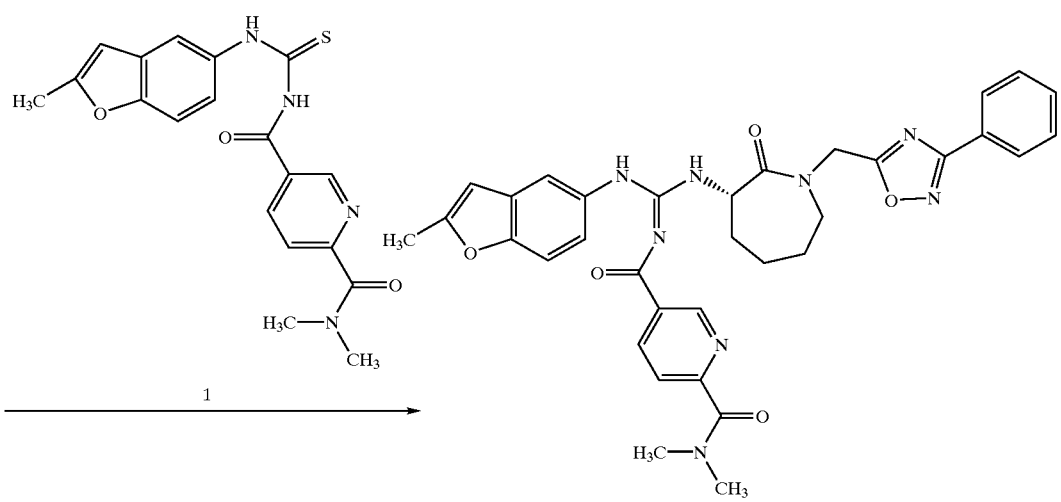

Part B compound ——————1——————>

Triethylamine (0.088 mL, 0.63 mmol) was added to a suspension of part B compound (57 mg, 0.20 mmol), 1 (71 mg, 0.18 mmol), and 1-[3-(dimethylamino)propyl]-3-ethylcarbodiimide hydrochloride (45 mg, 0.23 mmol) in tetrahydrofuran (0.64 mL). The reaction was stirred at ambient temperature overnight whereupon it was transferred to a separatory funnel with dichloromethane and water. The mixture was extracted with dichloromethane (2×). The combined organic layers were dried over magnesium sulfate and concentrated in vacuo to afford crude product. Flash chromatography (silica, 15 mm dia column, 3% methanol/dichloromethane) afforded the title compound (110 mg, 99%): HPLC (Method 1) $t_R$ 4.31 min, LRMS (ESI, pos ion spectrum) m/z 635 (M+H).

Using the procedure described in Example 12 the following compounds were prepared.

| Example | Structure | Characterization |
|---|---|---|
| 13 | 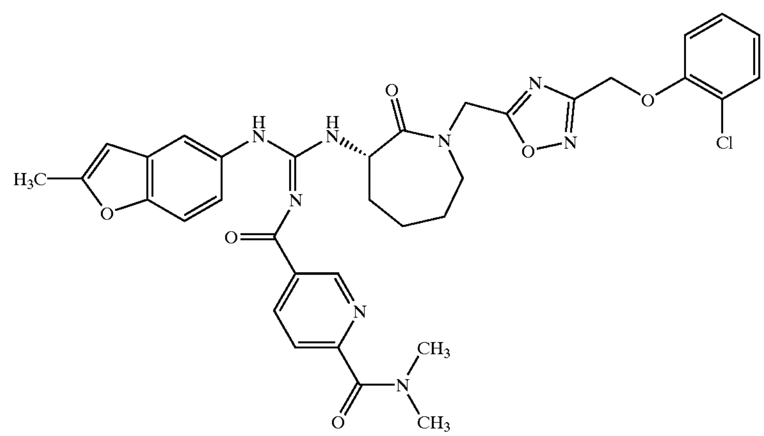 | HPLC (method 1) $t_R$ 4.3 min LRMS (ESI, pos ion spectrum) m/z 699/701 (M + H) |
| 14 | 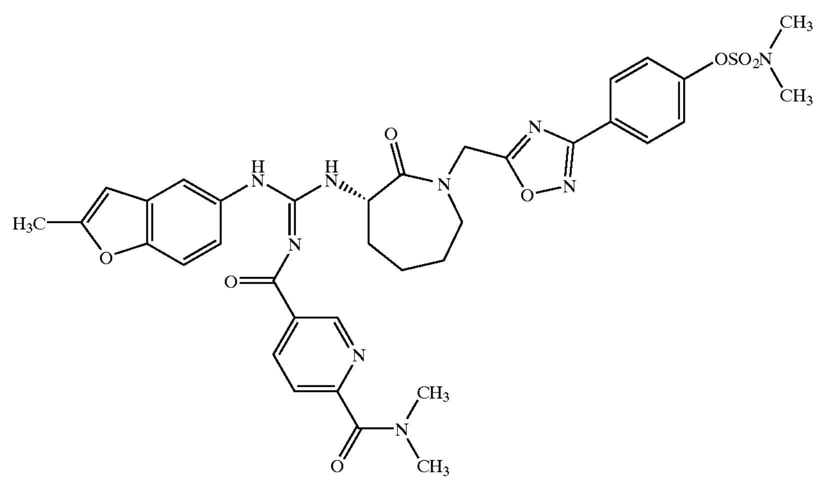 | HPLC (method 1) $t_R$ 4.2 min LRMS (ESI, pos ion spectrum) m/z 758 (M + H) |
| 15 | 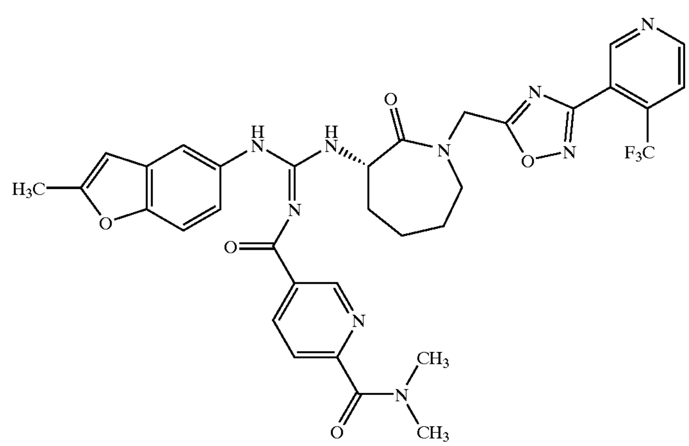 | HPLC (method 1) $t_R$ 4.1 min LRMS (ESI, pos ion spectrum) m/z 704 (M + H) |

-continued

| Example | Structure | Characterization |
|---|---|---|
| 16 | 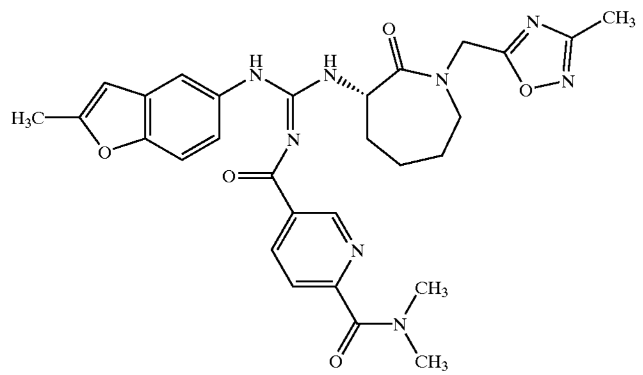 | HPLC (method 1) $t_R$ 3.8 min<br>LRMS (ESI, pos ion spectrum)<br>m/z 573 (M + H) |
| 17 | 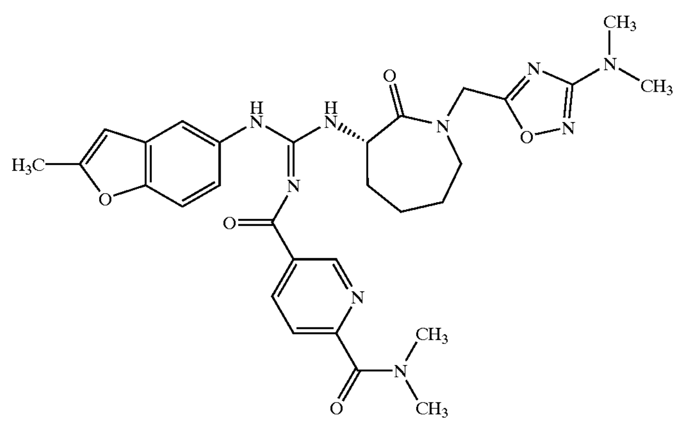 | HPLC (method 1) $t_R$ 3.9 min<br>LRMS (ESI, pos ion spectrum)<br>m/z 602 (M + H) |

EXAMPLE 18

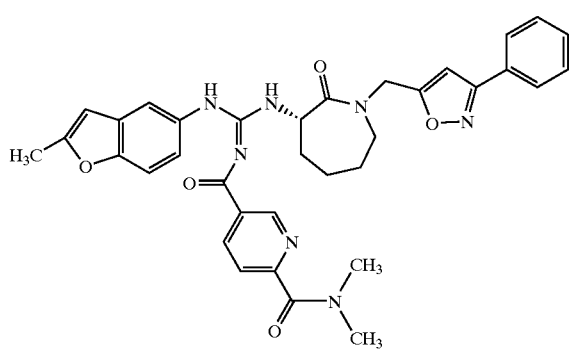

Part A:

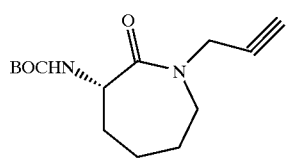

Lithium hexamethyldisilazide (1.0 N in THF, 8.0 mL, 8.0 mmol) in tetrahydrofuran (8 mL) was slowly added over 25 min to a stirring solution of 1,1-dimethylethyl [(3S)-hexahydro-2-oxo-1H-azepin-3-yl]carbamate (0.92 g, 4.0 mmol) in tetrahydrofuran (40 mL) at 0° C. under argon. After stirring at ambient temperature for 30 min, propargyl bromide (80% wt in toluene, 460 mg, 0.44 mL, 3.9 mmol) in tetrahydrofuran (4 mL) was added. After stirring overnight, the reaction was transferred to a separatory funnel with ethyl acetate and 5% potassium hydrogensulfate. The mixture was extracted with ethyl acetate (2×). The combined organic layers were washed with brine, dried over magnesium sulfate and concentrated in vacuo to afford 1.5 g of crude product. Flash chromatography (silica, 15 mm dia column, 50% ethyl acetate/hexane) afforded part A compound (0.85 g, 80%): HPLC (Method 1) $t_R$ 3.3 min; LCMS (ESI, pos ion spectrum, method 1) m/z 267 (M+H), $t_R$ 3.1 min.

Part B:

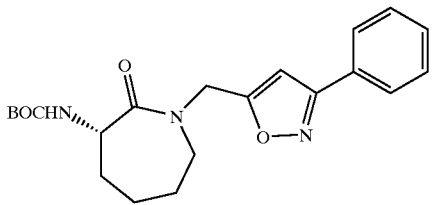

A solution of N-chlorosuccinimide (72 mg, 0.54 mmol), benzaldoxime (65 mg, 0.54 mmol), and pyridine (0.27 mL) in dichloromethane (2.0 mL) was refluxed for 1 hour. After cooling the reaction to ambient temperature, part A compound (0.15 g, 0.54 mmol) in dichloromethane (0.5 mL) was added followed by triethylamine (0.54 mL) in dichloromethane (0.25 mL). After refluxing an additional hour, the reaction was transferred to a separatory funnel with dichloromethane, washed with water, and dried over magnesium sulfate to afford 0.25 g of crude product after evaporation of the solvent. Flash chromatography (silica, 15 mm dia column, 20 to 50% ethyl acetate/hexane) afforded part B compound (58 mg, 28%): HPLC (Method 1) $t_R$ 3.9 min.

Part C:

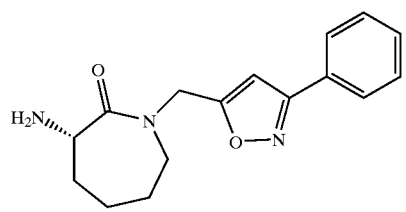

A solution of part B compound (58 mg, 0.15 mmol) in dichloromethane (0.50 mL) and trifluoroacetic acid (0.25 mL) was stirred at ambient temperature. After 1.5 h, the reaction was evaporated in vacuo. The residue was coevaporated with dichloromethane (2×), methanol and dichloromethane to afford crude product. This residue was taken up in methanol and added to a column of AG 50W-X2 (200–400 mesh, 1.4 g, prewashed with 5 mL each of methanol, water, and 1/1 methanol/water). The column was washed with methanol (5 mL) and eluted with 2 N ammonia in methanol to afford part C compound (34 mg, 80%): HPLC (Method 1) $t_R$ 2.3 min.

Part D:

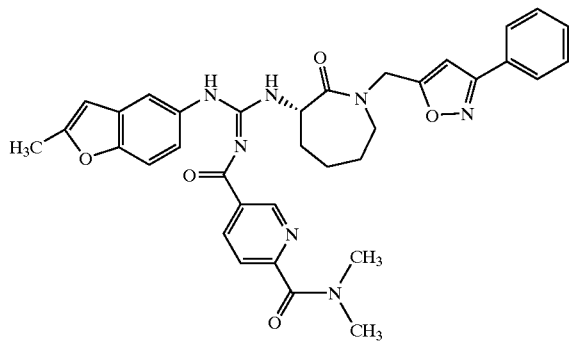

Triethylamine (0.052 mL, 0.37 mmol) was added to a suspension of part C compound (34 mg, 0.12 mmol), 1 (42 mg, 0.11 mmol), and 1-[3-(dimethylamino)propyl]-3-25 ethylcarbodiimide hydrochloride (26 mg, 0.13 mmol) in tetrahydrofuran (0.40 mL). After stirring at ambient temperature overnight, the reaction was transferred to a separatory funnel with dichloromethane and water. The mixture was extracted with dichloromethane (2×), dried over magnesium sulfate and concentrated in vacuo to afford the crude product. Flash chromatography (silica, 15 mm dia column, 3% methanol/dichloromethane) afforded the title compound (53 mg, 76%): HPLC (Method 1) $t_R$ 4.2 min; LRMS (ESI, pos ion spectrum) m/z 634 (M+H).

EXAMPLE 19

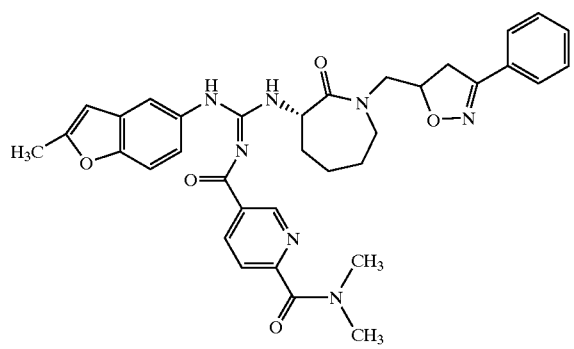

Part A:

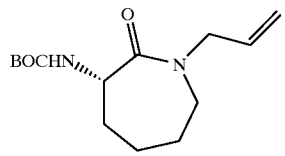

Lithium hexamethyldisilazide (1.0 N in THF, 8.0 mL, 8.0 mmol) in tetrahydrofuran (8 mL) was added over 25 min to a stirring solution of 1,1-dimethylethyl [(3S)-hexahydro-2-oxo-1H-azepin-3-yl]carbamate (0.92 g, 4.0 mmol) in tetrahydrofuran (40 mL) at 0° C. under argon. After stirring at ambient temperature for 30 min, allyl bromide (80% wt in toluene, 460 mg, 0.44 mL, 3.9 mmol) in tetrahydrofuran (4 mL) was added. After 2 days, the reaction was transferred to a separatory funnel with ethyl acetate and 5% potassium hydrogensulfate. The mixture was extracted with ethyl acetate (2×). The combined organic layers were washed with brine, dried over magnesium sulfate and concentrated to afford crude product. Flash chromatography (silica, 25 mm dia column, 25% ethyl acetate/hexane) afforded part A compound (1.0 g, 92%) : HPLC (Method 1) $t_R$ 3.5 min; LCMS (ESI, pos ion spectrum, method 1) m/z 269 (M+H), $t_R$ 3.1 min.

Part B:

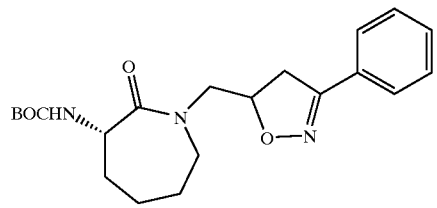

A solution of N-chlorosuccinimide (68 mg, 0.51 mmol), benzaldoxime (61 mg, 0.51 mmol), and pyridine (0.025 mL) in dichloromethane (2.0 mL) was refluxed for 1 hour. After cooling the reaction to ambient temperature, part A compound (0.14 g, 0.51 mmol) in dichloromethane (0.5 mL) was added followed by triethylamine (0.051 mL) in dichloromethane (0.25 mL). After refluxing an additional hour, the reaction was transferred to a separatory funnel with dichloromethane, washed with water, and dried over magnesium sulfate to afford 0.20 g of crude product after evaporation of the solvent. Flash chromatography (silica, 15 mm dia column, 40% ethyl acetate/hexane) afforded part B compound (120 mg, 61%): HPLC (Method 1) t$_R$ 3.8 min; LCMS (ESI, pos ion spectrum, method 2) m/z 388 (M+H), t$_R$ 1.7 min.

Part C:

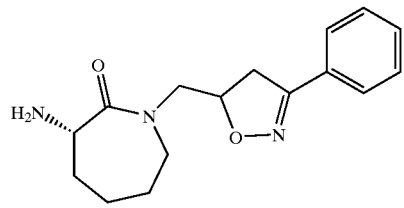

A solution of part B compound (120 mg, 0.30 mmol) in dichloromethane (0.90 mL) and trifluoroacetic acid (0.45 mL) was stirred at ambient temperature. After 2.5 h, the reaction was evaporated in vacuo. The residue was coevaporated with dichloromethane (2×), methanol and dichloromethane to afford crude product. This residue was then taken up in methanol and added to a column of AG 50W-X2 (200–400 mesh, 3.3 g, prewashed with 9 mL each of methanol, water, and 1/1 methanol/water). The column was washed with methanol (9 mL) and eluted with 2 N ammonia in methanol to afford part C compound (76 mg, 890): HPLC (Method 1) t$_R$ 2.1 and 2.2 min.

Part D:

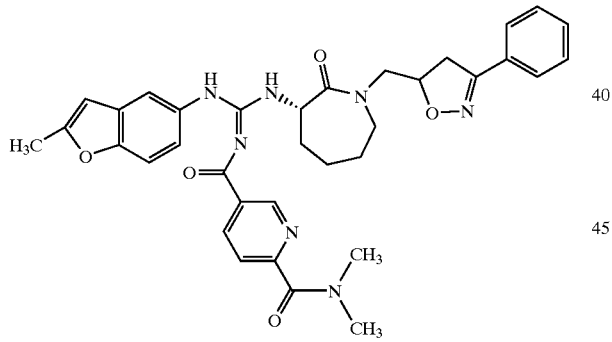

Triethylamine (0.11 mL, 0.80 mmol) was added to a suspension of part C compound (76 mg, 0.26 mmol), 1 (91 mg, 0.24 mmol), and 1-[3-(dimethylamino)propyl]-3-ethylcarbodiimide hydrochloride (56 mg, 0.28 mmol) in tetrahydrofuran (0.86 mL). After stirring at ambient temperature overnight, the reaction was transferred to a separatory funnel with dichloromethane and water. The mixture was extracted with dichloromethane (2×). The combined organic layers were dried over magnesium sulfate and concentrated in vacuo to afford crude product. Flash chromatography (silica, 15 mm dia column, 3% methanol/dichloromethane) afforded the title compound (130 mg, 85%): HPLC (Method 1) t$_R$ 4.2 min; LRMS (ESI, pos ion spectrum) m/z 636 (M+H).

What is claimed is:
1. A compound having the formula

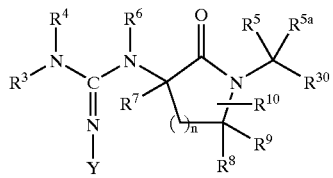

or a pharmaceutically acceptable salt thereof or all stereoisomers thereof, wherein n is 3;

Y is selected from hydrogen, alkyl, substituted alkyl, alkenyl, substituted alkenyl, alkynyl, substituted alkynyl, aryl, cycloalkyl, heteroaryl, cycloheteroalkyl, cyano, nitro, hydroxy, amino, —OR$_a$, —SR$_a$,

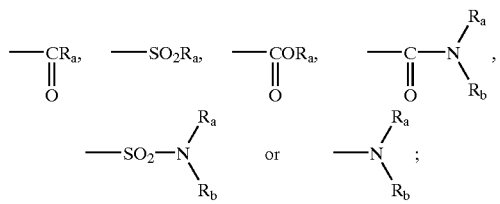

$R^4$, $R^6$, $R^8$, and $R^9$ are the same or different and are independently selected from hydrogen, alkyl, substituted alkyl, alkenyl, substituted alkenyl, alkynyl, substituted alkynyl, aryl, heteroaryl cycloheteroalkyl, cycloalkyl, alkylcarbonyl, arylcarbonyl, cycloalkylcarbonyl, substituted alkyl-carbonyl, cycloheteroalkylcarbonyl and heteroarylcarbonyl;

$R^3$ is hydrogen, alkyl, substituted alkyl, alkenyl, substituted alkenyl, alkynyl, substituted alkynyl, aryl, heteroaryl, cycloalkyl, cycloheteroalkyl, cyano, nitro, hydroxy, —OR$_a$, —SR$_a$,

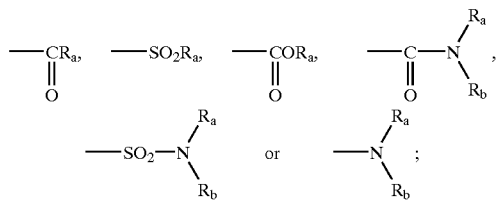

$R^5$, $R^{5a}$, and $R^7$ are the same or different and are independently selected from hydrogen, halogen, alkyl, substituted alkyl, alkenyl, substituted alkenyl, alkynyl, substituted alkynyl, heteroaryl, cycloalkyl, aryl, cycloheteroalkyl,

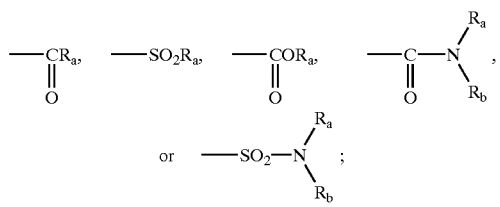

$R^{30}$ is alkyl, substituted alkyl, alkenyl, substituted alkenyl, alkynyl, substituted alkynyl, heteroaryl, cycloalkyl, aryl, cycloheteroalkyl, —C(O)thienyl, —C(O)furyl, or —C(O)aryl;

$R^{10}$ is selected from hydrogen, halogen, alkyl, substituted alkyl, alkenyl, substituted alkenyl, alkynyl, substituted alkynyl, aryl, heteroaryl, cycloalkyl, alkylcarbonyl, arylcarbonyl, cycloheteroalkyl, cycloalkylcarbonyl, substituted alkyl-carbonyl, cycloheteroalkylcarbonyl, heteroarylcarbonyl,

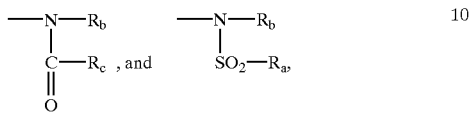

or when $R^9$ is hydrogen and $R^8$ and $R^{10}$ are on adjacent carbons they join to complete a cycloalkyl or phenyl ring;

$R_a$ and $R_b$ are the same or different and are independently selected from hydrogen, alkyl, substituted alkyl, alkenyl, substituted alkenyl, alkynyl, substituted alkynyl, aryl, heteroaryl, cycloheteroalkyl, cycloalkyl, alkylcarbonyl, arylcarbonyl, cycloalkylcarbonyl, substituted alkyl-carbonyl, cycloheteroalkylcarbonyl, heteroarylcarbonyl, aminocarbonyl, alkylaminocarbonyl and dialkylaminocarbonyl;

$R_c$ is hydrogen, halogen, alkyl, substituted alkyl, alkenyl, substituted alkenyl, aryl, heteroaryl, cycloalkyl, cycloheteroaryl,

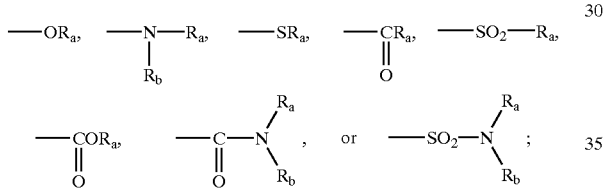

and wherein $R^3$ and $R^4$ and/or $R_a$ and $R_b$ can be taken together with the nitrogen to which they are attached to form a cycloheteroalkyl ring or a heteroaryl ring;

$R^3$ and Y can be taken together to form a heteroaryl ring;

$R^3$ or $R^4$ or Y can form a ring with $R^6$ which can be a cycloheteroalkyl or a heteroaryl ring;

$R^5$ and $R^{5a}$ can be taken together to the carbon to which they are attached to form a cycloalkyl ring, a heteroaryl ring or a cycloheteroalkyl ring, where one or more of $R^3$ $R^4$ or $R^6$ are H, then double bond isomers are possible;

the terms "substituted alkyl", "substituted alkenyl" and "substituted alkynyl" refer to such alkyl, alkenyl, and alkynyl groups having one, two, or three substituents selected from halo, alkoxy, haloalkoxy, cycloalkyl, cycloheteroalkyl, aryl, heteroaryl, arylcycloalkyl, aryloxy, arylalkoxy, heteroaryloxo, hydroxy, —$N_3$, nitro, cyano, $(R_{20})(R_{21})N$—, carboxy, thio, alkylthio, arylthio, arylalkylthio, heteroarylthio, alkyl-C(O)—, alkoxycarbonyl, $(R_{20})(R_{21})N$—C(O)—, arylcarbonyloxy, alkyl-C(O)—NH—, alkyl-C(O)—N(alkyl)—, aryl-C(O)—NH—, aryl-C(O)—N(alkyl)—, aryl-C(O)—, arylalkoxycarbonyl, alkoxycarbonyl-NH—, alkoxycarbonyl-N(alkyl)—, cycloalkyl-C(O)—, cycloheteroalkyl-C(O)—, heteroaryl-C(O)—, cycloalkyl-C(O)—NH—, cycloalkyl-C(O)—N(alkyl), cycloheteroalkyl-C(O)—NH—, cycloheteroalkyl-C(O)—N(alkyl)—, heteroaryl-C(O)—NH—, heteroaryl-C(O)—N(alkyl)—, arylsulfinyl, alkylsulfinyl, cycloalkylsulfinyl, cycloheteroalkylsulfinyl, heteroarylsulfinyl, arylsulfonyl, alkylsulfonyl, cycloalkylsulfonyl, cycloheteroalkylsulfonyl, heteroarylsulfonyl, $(R_{20})(R_{21})N$-sulfinyl, $(R_{20})(R_{21})N$-sulfonyl, alkyl-$SO_2$—NH—, alkyl-$SO_2$—N(alkyl)—, aryl-$SO_2$—NH—, N(alkyl)—, cycloalkyl-$SO_2$—NH—, cycloalkyl-$SO_2$—N(alkyl)—, cycloheteroalkyl-$SO_2$—NH—, cycloheteroalkyl-$SO_2$—N(alkyl)—, heteroaryl-$SO_2$—NH—, heteroaryl-$SO_2$—N(alkyl)—, $(R_{20})(R_{21})N$—C(O)—NH—, $(R_{20})(R_{21}C(O)$—N(alkyl)—, hydroxy-NH—C(O)—, hydroxy-N(alkyl)—C(O)—,

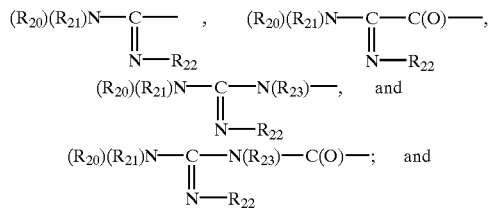

$R_{20}$, $R_{21}$, $R_{22}$, and $R_{23}$ are independently selected from hydrogen, alkyl, substituted alkyl, cycloalkyl, aryl, cycloheteroalkyl, and heteroaryl.

2. A compound of claim 1 wherein:

$R^3$ is hydrogen, alkyl, substituted alkyl, alkenyl, substituted alkenyl, aryl, heteroaryl or cycloheteroalkyl;

Y is cyano, nitro, aryl, heteroaryl, cycloheteroalkyl,

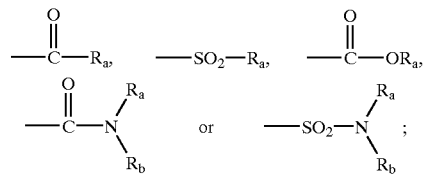

$R_a$ and $R_b$ are the same or different and are hydrogen, alkyl, substituted alkyl, alkenyl, substituted alkenyl, aryl, heteroaryl or cycloheteroalkyl;

$R^4$, $R^5$ $R^{5a}$, $R^6$, $R^7$, $R^8$, $R^9$ and $R^{10}$ are each hydrogen;

$R^{30}$ is alkyl, substituted alkyl, heteroaryl, —C(O)thienyl, —C(O) furyl, or —C(O) aryl; and the configuration at the chiral center is S— (as judged where $R^7$ is hydrogen).

3. A compound of claim 2 wherein:

$R^3$ is aryl;

Y is cyano or

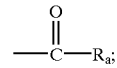

$R_a$ and $R_b$ are the same or different and are hydrogen, alkyl, aminocarbonyl, heteroaryl, aryl or cycloheteroalkyl;

$R^{30}$ is aryl, arylalkyl, —C(O)thienyl, —C(O) furyl, —C(O) aryl, substituted or unsubstituted isoxazol-5-yl, substituted or unsubstituted isoxazolin-5-yl, or substituted or unsubstituted 1,2,4-oxadiazol-5-yl-;

the configuration at the chiral center is S— (as judged where $R_7$ is hydrogen);

the terms unsubstituted isoxazol-5-yl", unsubstituted isoxazolin-5-yl", and "substituted 1,2,4-oxadiazol-5- yl" refer to a substituent attached to the available carbon atom selected from alkyl, substituted alkyl, alkoxy, alkylthio, keto, halo, hydroxy, cycloalkyl, aryl, cycloheteroalkyl, heteroaryl, $(R_{20})(R_{21})N—$, nitro, carboxy, cyano, alkoxycarbonyl, aryloxycarbonyl, alkylcarbonyl, substituted alkyl-C(O, arylcarbonyl, cycloalkylcarbonyl, $(R_{20})(R_{21})N—C(O)—$, guanidinylcarbonyl, $(R_{20})(R_{21})N—C(O)$alkyl-NH—C(O)—, $(R_{20})(R_{21})N—C(O)$-alkyl-N(alkyl)—C(O)—, alkyl-C(O)—NH—, alkyl-C(O)N(alkyl)—, substituted alkyl-C(O)—NH—, substituted alkyl-C(O)—N(alkyl)—, cycloalkyl-C(O)—NH—, cycloalkyl-C(O)—N(alkyl)—, aryl-C(O)—NH—, aryl-C(O)—N(alkyly, heteroaryl-C(O)—NH—, heteroaryl-C(O)—N(alkyl)—, cycloheteroalkyl-C(O)—NH—, cycloheteroalkyl-C(O)—N(alkyl)—, alkyl-$SO_2$—, substituted alkyl-$SO_2$—, aryl-$SO_2$—, cycloalkyl-$SO_2$—, cycloheteroalkyl-$SO_2$—, and heteroaryl-$SO_2$: and $R_{20}$ and $R_{21}$ are independently selected from hydrogen, alkyl, substituted alkyl, cycloalkyl, aryl, cycloheteroalkyl, and heteroaryl.

4. The compound of claim 3 wherein $R^3$ is substituted benzofuranyl.

5. A compound of claim 1 or a pharmaceutically acceptable salt thereof of the formula:

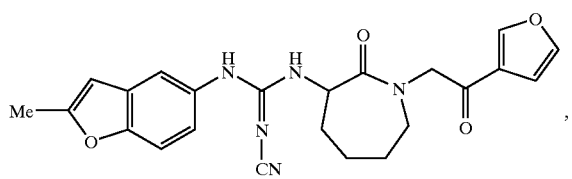

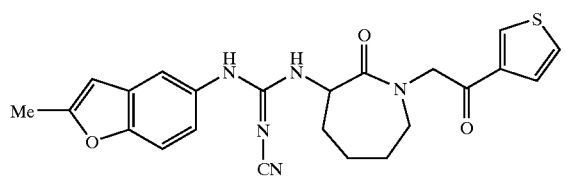

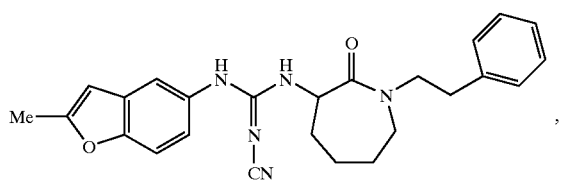

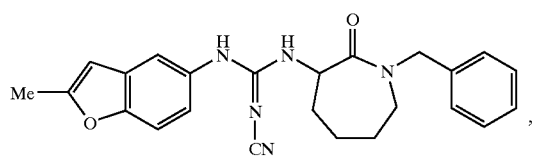

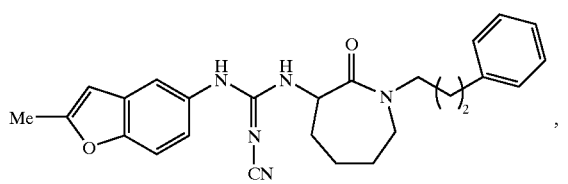

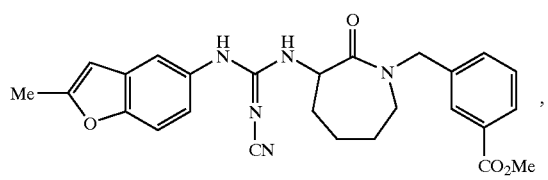

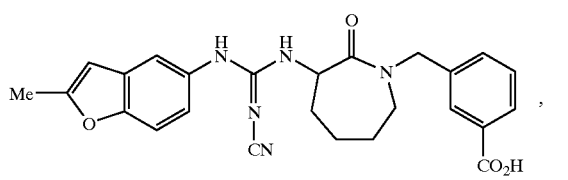

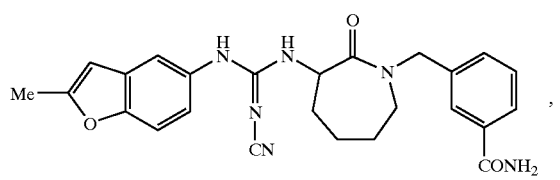

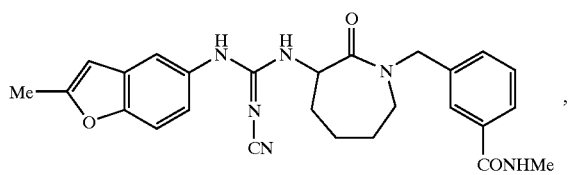

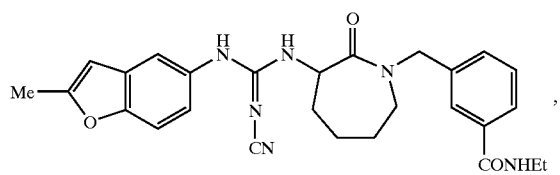

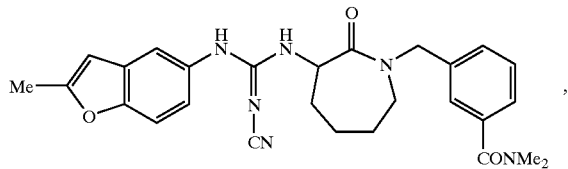

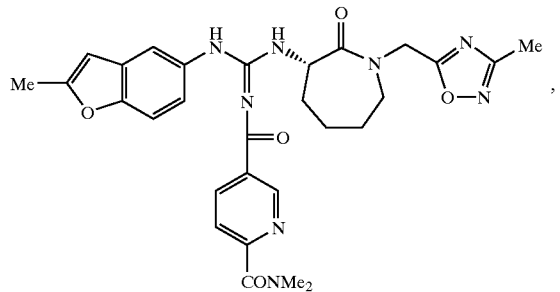

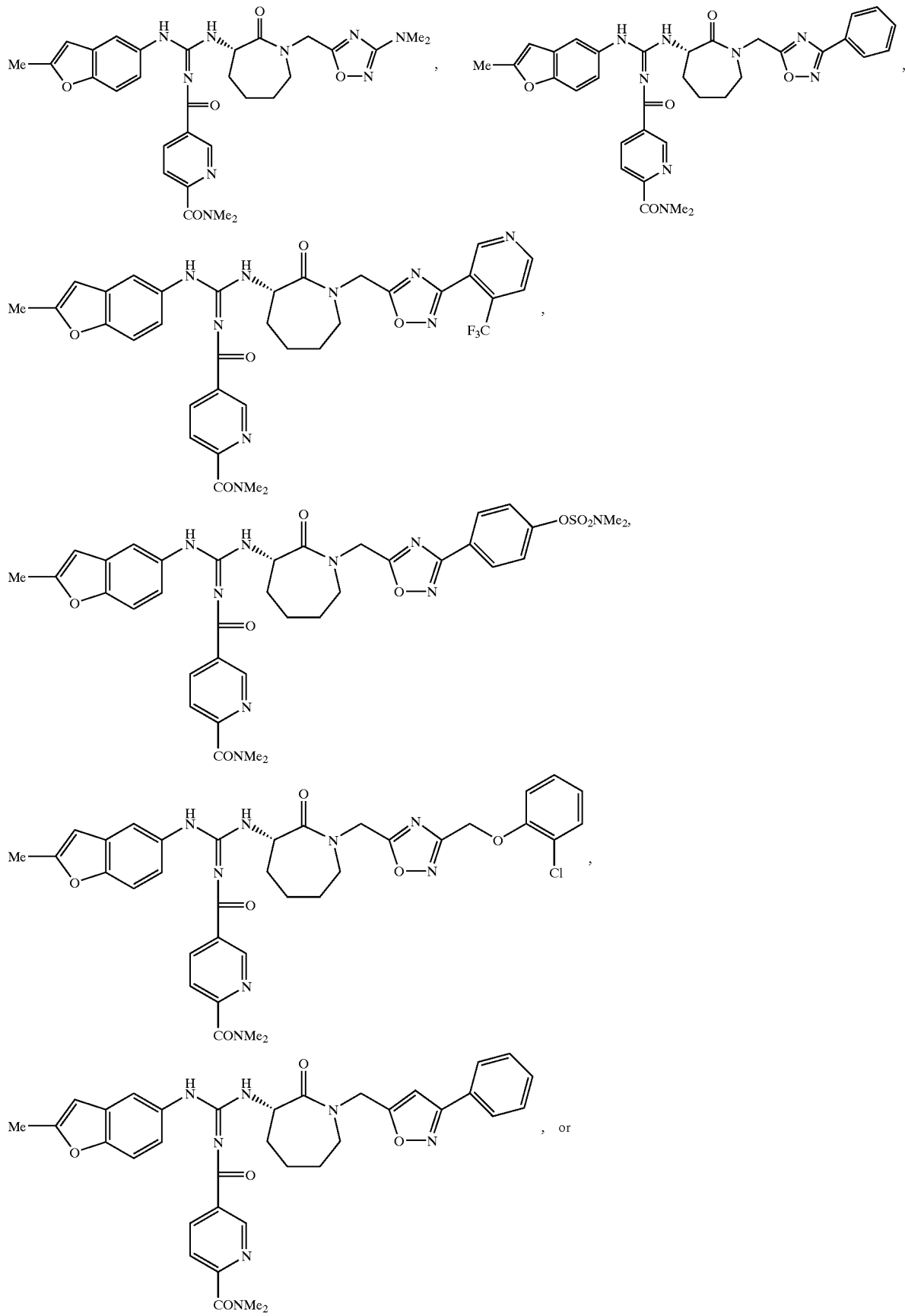

-continued

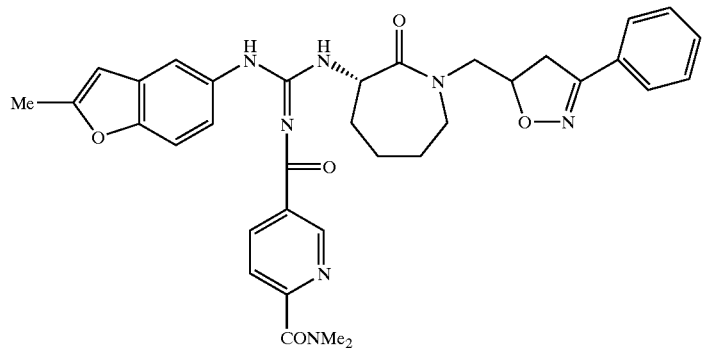

6. A pharmaceutical composition comprising a compound as defined in claim 1 and a pharmaceutically acceptable carrier therefor.

7. A method of treating a Factor Xa-associated disorder comprising administering an effective amount of at least one compound of claim 1 to a patient in need thereof wherein said Factor Xa-associated disorder is an acute coronary symdrome selected from myocardial infarction, unstable angina and non-Q Wave MI, thromembolic stroke, venous thrombosis, pulmonary embolism, peripheral occlusive consequences of surgery, interventional cardiology or immobility, the development of thrombosis on artificial surfaces, the thrombotic consequences of atherosclerotic vascular disease and/or atherosclerotic plaque rupture, coagulopathy including disseminated intravascular cooagulation, and the thromboembolic consequences of thrombophilia.

* * * * *